US008741347B2

(12) United States Patent
Laza-Knoerr et al.

(10) Patent No.: US 8,741,347 B2
(45) Date of Patent: Jun. 3, 2014

(54) METHOD FOR FORMING CYCLODEXTRIN POLYMER AND LIPOPHILIC COMPOUND EMULSIONS, RESULTING EMULSIONS, AND COMPOSITIONS INCLUDING SAID EMULSIONS

(75) Inventors: Anca-Lucia Laza-Knoerr, La Cheze (FR); Ruxandra Gref, Verrieres-le-Buisson (FR); Catherine Amiel, L'hay-les-Roses (FR); Patrick Couvreur, Villebon-sur-Yvette (FR)

(73) Assignees: Centre National de la Recherche Scientifique—CNRS, Paris (FR); Universite Paris—SUD 11, Orsay (FR)

( * ) Notice: Subject to any disclaimer, the term of this patent is extended or adjusted under 35 U.S.C. 154(b) by 8 days.

(21) Appl. No.: 13/265,550

(22) PCT Filed: Apr. 23, 2010

(86) PCT No.: PCT/FR2010/000330
§ 371 (c)(1),
(2), (4) Date: Jan. 4, 2012

(87) PCT Pub. No.: WO2010/122246
PCT Pub. Date: Oct. 28, 2010

(65) Prior Publication Data
US 2012/0107252 A1 May 3, 2012

(30) Foreign Application Priority Data

Apr. 23, 2009 (FR) .................................... 09 01983
Sep. 7, 2009 (FR) .................................... 09 56088

(51) Int. Cl.
| | |
|---|---|
| A61K 9/14 | (2006.01) |
| A61K 47/40 | (2006.01) |
| A61K 9/107 | (2006.01) |
| A61K 8/73 | (2006.01) |
| A61K 8/06 | (2006.01) |

(52) U.S. Cl.
CPC ................. *A61K 47/40* (2013.01); *A61K 9/107* (2013.01); *A61K 8/738* (2013.01); *A61K 8/06* (2013.01)
USPC ........................................................ 424/488

(58) Field of Classification Search
None
See application file for complete search history.

(56) References Cited

U.S. PATENT DOCUMENTS

2002/0019369 A1  2/2002  Li et al.
2005/0250881 A1* 11/2005  Gref et al. ..................... 523/440

FOREIGN PATENT DOCUMENTS

| EP | 0366154 A2 | 5/1990 |
|---|---|---|
| EP | 0875240 A2 | 11/1998 |

(Continued)

OTHER PUBLICATIONS

"Emulsion" Wikipedia definition (pp. 1-4, retrieved online on Aug. 2013).*

(Continued)

*Primary Examiner* — Bethany Barham
(74) *Attorney, Agent, or Firm* — Blank Rome LLP

(57) ABSTRACT

The present invention relates to a method for preparing a cyclodextrin polymer and/or a hydrophilic polymer emulsion having cyclodextrins as well as lipophilic compounds, the emulsions having a remarkable stability. In particular, the method includes: (i) adding a lipophilic compound into an aqueous solution of a cyclodextrin unit polymer or hydrophilic polymer having cyclodextrins; (ii) forming an emulsion from the mixture resulting from step (i). The invention also relates to the resulting emulsions, i.e. stabilized emulsions by a non-covalent and non-crystalline inclusion complex consisting of (i) a cyclodextrin unit polymer or a hydrophilic polymer having cyclodextrins and (ii) a lipophilic compound. The invention also relates to the use of said emulsions in the cosmetic, pharmaceutical and/or agri-food fields.

28 Claims, 22 Drawing Sheets

(56) References Cited

FOREIGN PATENT DOCUMENTS

JP    61227517 A    10/1986
WO    2008003685 A1    1/2008

OTHER PUBLICATIONS

Duchene, et al., "Cyclodextrins and emulsions," International Journal of Pharmaceutics, 2003, pp. 85-90, vol. 266, Elsevier B.V., Maryland Heights, MO, USA.

Ooya, et al., "Hydrogels having tubular alpha-cyclodextrin structure: effect of nano-tube structure on long alkyl chain partitions," Science and Technology of Advanced Materials, 2003, pp. 39-42, vol. 4, Elsevier Science Ltd., Maryland Heights, MO, USA.

Motoki, et al., English abstract only of "Emulsion preparation using beta-cyclodextrin and its derivatives acting as an emulsifier," Chemical & Pharmaceutical Bulletin, 2008, pp. 1335-1337, vol. 56, No. 9, Nihon University, Tokyo, Japan.

* cited by examiner (a)

(b)

METHOD FOR FORMING CYCLODEXTRIN POLYMER AND LIPOPHILIC COMPOUND EMULSIONS, RESULTING EMULSIONS, AND COMPOSITIONS INCLUDING SAID EMULSIONS

CROSS-REFERENCE TO RELATED APPLICATION

The present application claims the benefit of International Patent Application No. PCT/FR2010/000330, filed Apr. 23, 2010, which in turn claims priority to French Patent Application Nos. FR0901983, filed Apr. 23, 2009, and FR0956088, filed Sep. 7, 2009, the entire disclosures of which are incorporated by reference herein.

TECHNICAL FIELD

The present invention relates to a method for preparing emulsions based, on the one hand, on cyclodextrin polymers and/or on hydrophilic polymers bearing cyclodextrins and, on the other hand, on lipophilic compounds, the emulsions having a remarkable stability. The invention also relates to the resulting emulsions, i.e. emulsions stabilized by a non-covalent and non-crystalline inclusion complex made up (i) of a cyclodextrin unit-based polymer or of a hydrophilic polymer bearing cyclodextrins and (ii) of a lipophilic compound. The invention also relates to the use of these emulsions in the cosmetics, agri-food industry or pharmaceutical field.

In the description below, the references between square brackets ([ ]) refer back to the list of references provided after the examples.

BACKGROUND ART

Emulsions are very widely used in numerous technical fields, simply due to the fact that they allow long-lasting dispersion of at least two liquid-liquid immiscible phases generally by means of a surface agent (surfactant).

There are two major categories of emulsions: oil-in-water emulsions (emulsions obtained by the direct route) and water-in-oil emulsions (emulsions obtained by the inverse route). In the first case, the continuous phase is the water (droplets of oil are dispersed in this phase); and in the second case, the continuous phase is the oil wherein droplets of water are dispersed. The type of a simple, direct or inverse emulsion is fixed in the first order by the preferential solubility of the surfactant in one or other phase. Recourse to a water-soluble surfactant makes it possible to preferentially form a direct emulsion, whereas a liposoluble surfactant promotes an inverse emulsion.

Numerous cosmetic compositions are prepared from emulsions (typically simple emulsions) stabilized by surfactants.

For example, EP 0 685 227 [1] proposes a very complex system of sunscreen cosmetic compositions, of the type comprising an aqueous continuous phase, a protective system capable of filtering UV rays (Parsol® MCX, $TiO_2$, benzophenone derivatives, etc.), a surfactant, organic solvents (lower polyols and alcohols) and at least one polymer or more particularly one crosslinked copolymer (alkyl acrylates, vinyl acetate).

FR 2 858 777 [2], for its part, proposes a stable oil-in-water emulsion containing at least one fatty substance (fatty acid esters, waxes, butters, natural—plant, animal, of marine origin—oils, synthetic oils or mineral oils, hydrogenated oils and mixtures thereof), at least one surfactant (fatty acid esters of polyglycerol, such as the ethoxylated compounds, ethoxylates of alcohols), at least one cosurfactant (polyols), and water.

However, the use of surfactants in products intended to be administered to humans (whether in topical form, oral form, or the like) can be a problem. This is because surfactants can damage cell membranes. Thus, in particular in the cosmetics field, efforts have been made to reduce the potentially harmful effects of surfactants, or even to eliminate recourse to surfactants.

In this perspective, recourse to cyclodextrins has been considered.

For example, Duchêne et al. ("Cyclodextrins and emulsions", *International Journal of Pharmaceutics*, 266 (2003), 85-90 [3]) and Yu et al. ("Effect of camphor/cyclodextrin complexation on the stability of O/W/O multiple emulsions", *International Journal of Pharmaceuticals*, 261 (2003), 1-8 [4]) have proposed the formulation of multiple emulsions using α-, β- and γ-cyclodextrin monomers as stabilizing agent. Two of the cyclodextrins (α-, β-) exhibit stabilizing properties during the preparation of a multiple (double) emulsion; the larger cavity of γ-cyclodextrin being unfavorable to stabilization owing to its size which is too great to result in an optimum interaction with alkyl chains.

Other emulsions based on cyclodextrin monomers have also been proposed by Inoue et al. ("Emulsion preparation using β-cyclodextrin and its derivatives acting as an emulsifier", *Chem. Pharm. Bull*, 56 (9), (2008), 1335-1337 [5], "Formulation and characterisation of emulsions using β-cyclodextrin as an emulsifier", *Chem. Pharm. Bull*, 56 (5), (2008), 668-671, [6] and "Preparation and characterisation of n-alkane/water emulsion stabilized by cyclodextrin", *Journal of oleo science*, 58, (2), (2009), 85-90, [7]). The results indicate that, on the one hand, the addition of a cyclodextrin (α-, β- and γ-monomer) leads to the formation of a precipitate and, on the other hand, the adsorption of said precipitate at the oil-water interface is necessary in certain cases in order to stabilize emulsions.

Document WO 2008/003685 [8] proposes an emulsion based on optionally modified cyclodextrin monomers, a modified polysaccharide, a fatty substance and water.

In any event, an emulsion can be prepared, but the cyclodextrin monomers do not make it possible to stabilize it in a long-lasting manner (a precipitate forms).

There is therefore a need to develop methods capable of stabilizing emulsions without having recourse to surfactants.

DESCRIPTION OF THE INVENTION

Entirely unexpectedly and surprisingly, the inventors have discovered that it is possible to prepare remarkably stable emulsions without having to use, for this, organic solvents, surfactants, cosurfactants or other synthetic organic additives.

More specifically, the inventors have discovered that the use of a non-covalent and non-crystalline inclusion complex made up (i) of a cyclodextrin unit-based polymer I or of a hydrophilic polymer II bearing cyclodextrins and (ii) of a lipophilic compound makes it possible to obtain an emulsion of remarkable stability.

Emulsions based on cyclodextrins (monomers) and on lipophilic compounds in an aqueous medium have already been described. In this respect, it is in particular known that, if cyclodextrins and a lipophilic compound are brought together in an aqueous medium, the formation of inclusion complexes between the lipophilic parts of said compound and the cyclodextrins is observed.

However, up until now, these inclusion complexes have always been described as having a crystalline nature, which facilitates precipitation of the complex and results in an emulsion of inefficient stability for applications on the industrial scale, such as in the cosmetics field, the pharmaceutical field and the agri-food industry.

Aqueous solutions of a lipophilic compound containing cyclodextrin oligomers have also been reported. For example, document JP 61/227,517 describes such solutions, based on poly-beta-cyclodextrin trimers or tetramers (i.e. cyclodextrin compounds of low molecular weight which are therefore very soluble in water). However, this document does not envision the preparation of an emulsion. Moreover, the inventors have demonstrated that such oligomers cannot be used to form simple or multiple oil-in-water and water-in-oil emulsions, and that only cyclodextrin polymers are effective for preparing such emulsions. The inventors have, moreover, surprisingly demonstrated that cyclodextrin unit-based polymers (e.g. poly α-, β- and/or γ-cyclodextrins) or hydrophilic polymers bearing cyclodextrins (e.g. polysaccharides onto which cyclodextrins are grafted) are not only very effective for forming such emulsions, but also that the latter have a remarkable stability.

The present invention is based on the entirely unexpected discovery of the possibility of forming inclusion complexes between cyclodextrin unit-based polymers (e.g. poly α-, β- and/or γ-cyclodextrins) or hydrophilic polymers bearing cyclodextrins (e.g. polysaccharides onto which cyclodextrins are grafted) and lipophilic compounds, which complexes can perform the function of "surfactants" as such owing to their amphiphilic nature, and can stabilize emulsions in a remarkable manner.

Thus, one aspect of the invention is to provide compositions comprising an emulsion free of any traces of surfactants, that can advantageously replace the compositions known in the art for vectorizing active ingredients or cosmetic products. In this context, one of the objects of the invention is based on the encapsulation of lipophilic compounds of interest for the preparation of compositions having at least one of the following properties:
- toning down, or even masking, the odor of a lipophilic compound contained in the emulsion (e.g., lavandin essential oil),
- toning down, or even masking, the unpleasant taste of a lipophilic compound contained in the emulsion (e.g., fish oil),
- improving stability for readily oxidizable lipophilic compounds (e.g., borage oil),
- preservation of stability for readily volatile lipophilic compounds (e.g., beta-alanine ester, fragrance),
- increase in solubility for insoluble lipophilic compounds (e.g., ginger oil, geraniol).

One object of the invention is also to provide surfactant-free emulsions which nevertheless have sufficient stability to be able to be stored for a period at least of about a few weeks, or even a few months.

Thus, according to one aspect of the invention, there is provided a simple or multiple emulsion, characterized in that it is stabilized by a non-covalent and non-crystalline inclusion complex made up (i) of a cyclodextrin unit-based polymer I or of a hydrophilic polymer II bearing cyclodextrins and (ii) of a lipophilic compound.

Advantageously, the cyclodextrin unit-based polymer and the hydrophilic polymer bearing cyclodextrins contain at least 10 cyclodextrin units, preferably at least 15 cyclodextrin units, and advantageously at least 20 cyclodextrin units. Particularly advantageously, it is preferred for the cyclodextrin unit-based polymers and hydrophilic polymers bearing cyclodextrins to comprise, on average, at least 100 cyclodextrin units, preferably at least 200 cyclodextrin units, and advantageously at least 300 cyclodextrin units. Typically, the cyclodextrin unit-based polymers and hydrophilic polymers bearing cyclodextrins comprise, on average, at least 400 cyclodextrin units.

Advantageously, the cyclodextrin unit-based polymer and the hydrophilic polymer bearing cyclodextrins contain, on average, between 10 and 1500 cyclodextrin units within their structure, preferably, on average, between 10 and 1000 cyclodextrin units, preferably, on average, between 15 and 800 cyclodextrin units, preferably, on average, between 50 and 600 cyclodextrin units, and advantageously, on average, between 100 and 400 cyclodextrin units.

According to certain embodiments, the cyclodextrin unit-based polymer and the hydrophilic polymer bearing cyclodextrins that are used in the context of the present invention have a higher molar mass. For example, the cyclodextrin unit-based polymer and the hydrophilic polymer bearing cyclodextrins can comprise, on average, between 10 and 2000 cyclodextrin units within their structure, preferably, on average, between 100 and 1800 cyclodextrin units, preferably, on average, between 500 and 1600 cyclodextrin units, and advantageously, on average, between 800 and 1500 cyclodextrin units.

The term "hydrophilic polymer bearing cyclodextrins", as used herein, refers to a hydrophilic polymer onto which cyclodextrin monomers are grafted. In other words, it is a hydrophilic polymer to which cyclodextrin monomers are attached by covalent bonding. These cyclodextrin monomers may be identical or different on the same hydrophilic polymer.

The hydrophilic polymer may be any neutral, cationic or anionic hydrophilic polymer. For example, it may be a hydrophilic polymer commonly used in the formulation of pharmaceutical, cosmetic and/or agri-food compositions. For example, aqueous dispersions of polymer are commonly used in the pharmaceutical industry for film-coating galenical forms intended for oral administration and for allowing controlled release of the active ingredient. Hydrophilic polymers are increasingly used for their ability to retain water, their film-forming nature and the fact that they stay at the surface of the skin without the ability to penetrate. By way of example, polysaccharides (such as sodium alginate, propylene glycol alginate), galactomannans (aloe gel, guar gum), xanthan gum (Rhodopol®), cellulose derivatives (such as hydroxyethylcellulose, hydropropylcellulose, hydropropylmethylcellulose, methylcellulose or carboxymethylcellulose); acrylic and vinyl polymers (such as carbomers or Carbopols®, Acrysols®, cyanoacrylic polymers, polyvinylpyrrolidone or povidone); polyvinyl alcohols; polyethylene glycols; or polyquaterniums may be cited.

Silicone polymers (such as poly(methylhydrosiloxane) or poly(methylhydrosiloxane-co-dimethylsiloxane)) are not considered to be hydrophilic polymers II according to the present invention.

The emulsion may be a simple or multiple, oil-in-water or water-in-oil emulsion. It is preferably a simple oil-in-water emulsion.

The polymer I or II can be chosen from the group comprising:
- poly-α-, poly-β- or poly-γ-cyclodextrins,
- copolymers of α-, β- and/or γ-cyclodextrins,
- natural or synthetic polymers onto which α-, β- and/or γ-cyclodextrins are grafted,
- or a mixture thereof;

wherein the α-, β- and/or γ-cyclodextrin units are optionally modified.

In particular, the polymer I or II can be chosen from the group comprising:
- poly-β-cyclodextrins,
- poly-γ-cyclodextrins,
- polysaccharides onto which β-cyclodextrins and/or γ-cyclodextrins are grafted,
- or a mixture thereof.

The cyclodextrin unit-based polymers I comprise, on average, at least 10 cyclodextrin units, preferably at least 15 cyclodextrin units, and advantageously at least 20 cyclodextrin units. Particularly advantageously, it is preferred for the cyclodextrin unit-based polymers to comprise, on average, at least 100 cyclodextrin units, preferably at least 200 cyclodextrin units, and advantageously at least 300 cyclodextrin units. Typically, the cyclodextrin unit-based polymers comprise, on average, at least 400 cyclodextrin units.

The average number of cyclodextrin units present in the polymers of an emulsion of the invention can, for example, be established by size exclusion chromatography and by nuclear magnetic resonance.

Generally, the cyclodextrin unit-based polymer I comprises, on average, between 10 and 1500 cyclodextrin units within its structure, preferably, on average, between 10 and 1000 cyclodextrin units, preferably, on average, between 15 and 800 cyclodextrin units, preferably, on average, between 50 and 600 cyclodextrin units, and advantageously, on average, between 100 and 400 cyclodextrin units.

According to certain embodiments, the polymers I used in the context of the present invention have a higher molar mass. For example, the cyclodextrin unit-based polymer I can comprise, on average, between 10 and 2000 cyclodextrin units within its structure, preferably, on average, between 100 and 1800 cyclodextrin units, preferably, on average, between 500 and 1600 cyclodextrin units, and advantageously, on average, between 800 and 1500 cyclodextrin units.

The cyclodextrin units present within the polymers I or II can generally be α-cyclodextrins, β-cyclodextrins, γ-cyclodextrins, or else mixtures of at least two of these types of cyclodextrins. Advantageously, the cyclodextrin units present in the polymers I or II preferably comprise β-cyclodextrins and/or γ-cyclodextrins. According to one particular variant, all the cyclodextrin units present in the polymers I or II are β-cyclodextrins. According to another particular variant, all the cyclodextrin units present in the polymers I or II are γ-cyclodextrins.

Within the cyclodextrin unit-based polymers I, the cyclodextrin units are generally bound to one another via linear or branched hydrocarbon chains containing from 3 to 50 carbon atoms, optionally interrupted with one or more oxygen atoms, these chains preferably being alkyl, alkenyl or alkynyl chains containing from 3 to 50 carbon atoms, or else polyether chains containing from 3 to 50 carbon atoms, it being possible for these chains to be substituted with hydrophilic groups (hydroxyl groups, for example). The chains binding the cyclodextrin units to one another contain at least 3 carbon atoms and preferably from 4 to 50 carbon atoms, the shortest path between two cyclodextrin units preferably consisting of a chain containing between 3 and 8 carbon atoms.

Advantageously, the hydrocarbon chains which link two cyclodextrin units to one another within a cyclodextrin unit-based polymer I correspond to the general formula a group of formula —O—$(CH_2-CHOR^1-CH_2)_n$—O—, where n is an integer between 1 and 50 (generally between 2 and 10) and where, in each of the n units $(CH_2-CHOR^1-CH_2)$, $R^1$ denotes either a hydrogen atom or a —$CH_2$—CHOH—$CH_2$—O— chain bound to a cyclodextrin unit of the polymer.

Thus, the polymers I can typically be obtained by crosslinking of cyclodextrin molecules with bifunctional compounds capable of forming covalent bonds with the hydroxyl groups of the cyclodextrins. For example, they may be dicarboxylic acids such as citric acid, sebacic acid, fumaric acid, glutamic acid, maleic acid, malic acid, malonic acid, oxalic acid, succinic acid, glutaric acid, terephthalic acid, isophthalic acid, oxaloacetic acid, phthalic acid, adipic acid or butanedioic acid.

For example, the polymers I can be obtained by polycondensation of cyclodextrin and epichlorohydrin molecules, generally in a basic medium (generally in an aqueous medium to which sodium hydroxide has been added, at a concentration by weight of 10 to 40%), the cyclodextrin/epichlorohydrin molar ratio preferably being between 1:15 and 1:1, and advantageously between 1:15 and 1:8. For further details concerning this synthesis and control of the average number of cyclodextrin units integrated into the cyclodextrin unit-based polymers obtained according to this method, reference may in particular be made to the following articles:

E. Renard et al., European Polymer Journal, vol. 33, No. 1, pp 49-57 (1997) [9]

Gref et al., International Journal of Pharmaceutics, vol. 332, issues 1-2, pages 185-191 (2007) [10]

Gref et al., J. Control Release, 111(3): 316-24 (2006) [11]

Gref et al., Journal of colloid and interface science, 307(1): 83-93 (2007) [12]

Blanchemain et al., Acta Biomaterialia, volume 4 issue 6, November 2008, pages 1725-1733 [13].

The polymers I can also be obtained by polycondensation of cyclodextrin and hexamethylene diisocyanate molecules, as described, for example, in Elif Yilmaz Ozmen et al. *Bioresource Technology*, volume 99, issue 3, pages 526-531 (2008) [14].

The polymers I can also be obtained by polycondensation of cyclodextrin molecules and a functionalized polyethylene glycol, as described, for example, in:

Cesteros et al., *European Polymer Journal*, volume 45, issue 3, pages 674-679 (2009) (acyl PEG) [15]

Salmaso et al., *International Journal of Pharmaceutics*, volume 345, issues 1-2, pages 42-50 (2007) (diamino PEG) [16].

The polymers I can also be obtained by polycondensation of cyclodextrin molecules and several oligoethylimine branches, so as to form a star polymer, as described, for example, in Yang et al., *Biomaterials*, volume 28, issue 21, pages 3245-3254 (2007) [17].

Whichever may be the exact nature of the hydrocarbon chains binding the cyclodextrin units to one another, generally, the total weight of the cyclodextrin units present within the polymers I represents at least 30%, advantageously at least 40%, and even more preferentially at least 50%, of the total weight of said polymers, this total weight of the cyclodextrin units generally representing between 30 and 80%, and preferably between 40 and 75%, of the total weight of the cyclodextrin unit-based polymers.

This weight percentage of cyclodextrins in the polymers that can be used in the context of the present invention can be determined, for example, by nuclear magnetic resonance (NMR).

Moreover, the polymer I present in an emulsion according to the invention generally has a number-average molar mass of between 10 000 and 3 000 000 g/mol, advantageously between 20 000 and 2 000 000, and preferably between 100 000 and 1 500 000 g/mol.

Advantageously, the polymer I present in an emulsion according to the invention has a number-average molar mass greater than or equal to 100 000 g/mol. This makes it possible to achieve emulsions of particularly high stability.

Advantageously, the polymer I can have the lowest possible polydispersity index (i.e. ratio of the weight-average molar mass to the number-average molar mass), preferably less than 3, and even more advantageously less than 2.

In certain embodiments, the polymer I can be a poly-β-cyclodextrin corresponding to the following formula I:

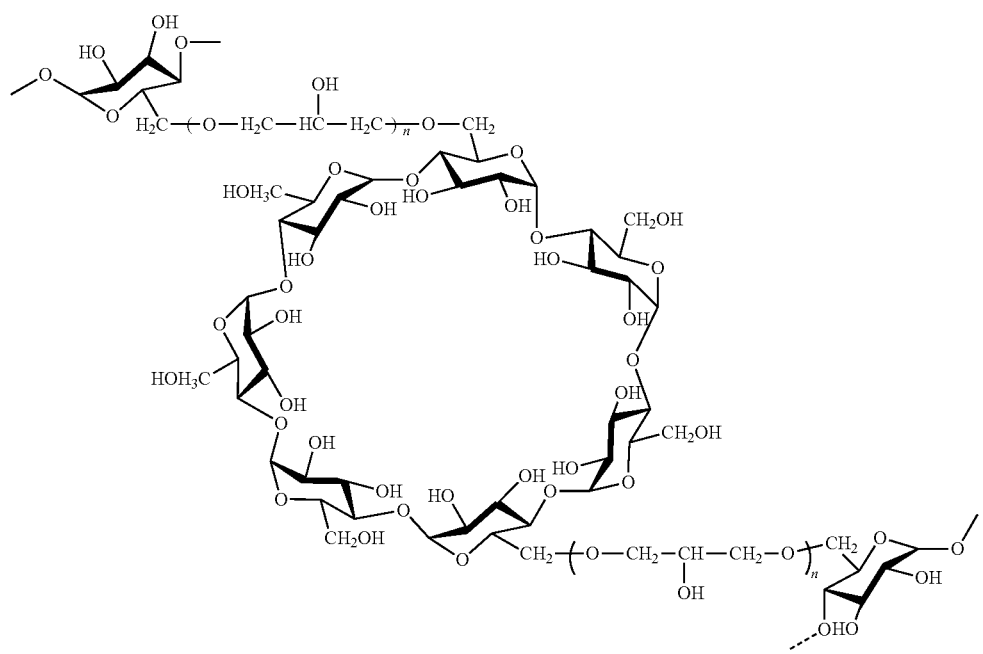

Formula I wherein n represents an integer between 1 and 50, preferably between 2 and 10; and the number of beta-cyclodextrin units is, on average, between 10 and 1500, preferably, on average, between 10 and 1000, preferably, on average, between 15 and 800, preferably, on average, between 50 and 600, and advantageously, on average, between 100 and 400 units.

In the above structure, the monosaccharides at the ends of the structure (i.e. with bonds represented as dashed lines) represent diagrammatically the continuity of the polymer (i.e. succession of β-cyclodextrin units forming the rest of the polymer).

In certain embodiments, the polymer I can be a poly-β-cyclodextrin of higher molar mass, and can correspond to formula I above, wherein n represents an integer between 1 and 50, preferably between 2 and 10; and the number of beta-cyclodextrin units is, on average, between 10 and 2000, preferably, on average, between 100 and 1800 units, preferably, on average, between 500 and 1600, and advantageously, on average, between 800 and 1500 units.

In certain embodiments, the polymer I can be a poly-α-cyclodextrin corresponding to formula I above, wherein the β-cyclodextrin units are replaced with α-cyclodextrins.

In certain embodiments, the polymer I can be a poly-γ-cyclodextrin corresponding to formula I above, wherein the β-cyclodextrin units are replaced with γ-cyclodextrins.

The polymer II can be a synthetic or natural, generally hydrophilic polymer. It can, for example, be a polysaccharide. For example, it can be hyaluronic acid, alginic acid, chitosan, chitin, scleroglucan, dextran, amylose, amylopectin, a cellulose derivative, starch, pullulan, pectin, an alginate, heparin, ulvan, a carrageenan, fucan, curdlan, xylan, polyguluronic acid, xanthan, arabinan, or polymannuronic acid. Advantageously, the hydrophilic polymer II can be hyaluronic acid. Indeed, the latter can be advantageous, in particular for emulsions for cosmetic purposes, owing to its bioadhesion properties. Thus, a composition comprising an emulsion according to the invention based on hyaluronic acid bearing cyclodextrins may make it possible to reinforce, or in any event prolong, the desired cosmetic effect, since the droplets of the emulsion will have a greater tendency to remain at the surface of the skin (owing to the bioadhesive properties of hyaluronic acid).

The hydrophilic polymer II can be optionally modified, i.e. some of its groups can have undergone a chemical transformation. For example, the hydrophilic polymer II can be a natural sulfated polysaccharide such as chondroitin sulfate, fucoidan or heparan sulfate. Heparan sulfate is an endogenous glycan that is bioactive in humans; fucoidan is also a sulfated polysaccharide, but of marine origin and extracted from brown algae. Fucoidan has activities on mammalian biological systems which could make it a substitute for sulfated polysaccharides of animal origin used in therapy (heparin). Fucoidan is among the most powerful inhibitors of the Complement system, which plays a major role in the defense mechanisms of the organism. The Complement is activated at the beginning of any attack on a tissue, and constitutes an early defense mechanism during the immune reaction. However, uncontrolled Complement activation can be responsible for tissue damage, as in transplant rejection, inflammatory pathological conditions and certain neurodegenerative pathological conditions such as Alzheimer's disease. Fucoidan blocks complement by inhibiting the two pathways of classical and alternative activation of the Complement system.

Alternatively, natural polysaccharides can be sulfated. This can be carried out, for example, by enzymatic conversion (WO 2006/124801) [18]. Alternatively, these polysaccharides can be extracted from natural sources, such as certain algae, for instance *Durlillaea antartica*, or green algae of the Ulva family (Ulva and *Enteromorpha* sp) having intrinsic beneficial properties (skin healing). Alternatively, the polysaccharide may naturally contain sulfate groups. Heparin and ulvan, for example, may be cited.

Methods for grafting cyclodextrins to natural or synthetic polymers, in particular polysaccharides, are known. For example, those skilled in the art may take inspiration from the methods described in:

β-Cyclodextrins Grafted onto Chitosan:

Prabaharan et al., *International Journal of Biological Macromolecules*, volume 44, issue 4, pages 320-325 (2009) [19]

Zhang et al., "Chitosan bearing pendant cyclodextrin as a carrier for controlled protein release", *Carbohydrate Polymers, In Press, Corrected Proof, Available online Jan.* 30, 2009 [20].

It is understood that the hydrophilic polymer II bearing cyclodextrins can be chemically modified by using conventional synthetic techniques known to those skilled in the art. Reference may be made, for example, to:

Prabaharan et al., *Carbohydrate Polymers*, volume 73, issue 1, pages 117-125 (2008) [21]

Prabaharan et al., *Carbohydrate Polymers*, volume 73, issue 1, pages 117-125 (2008) [22]

which describe the functionalization of a carboxymethyl chitosan β-cyclodextrin with the methyl ester of cysteine, resulting in a sulfurized version (—SH) of the polymer which has improved mucoadhesive properties.

A copolymer of cyclodextrin units and another monomer may also be considered, as described, for example, in Lu et al., *European Polymer Journal*, volume 44, issue 7, pages 2140-2145 (2008) (radical copolymerization of polylactic acid and of vinyl derivatives of β-cyclodextrins) [23].

A cyclodextrin unit-based polymer (polymer I) grafted onto another polymer may also be considered, as described, for example, in Blanchemain et al., *Acta Biomaterialia*, volume 4, issue 5, pages 1392-1400 (2008) [24], or crosslinked with a polysaccharide, as described, for example, in Zha et al., *Journal of Membrane Science*, volume 321, issue 2, pages 316-323 (2008) [25].

The emulsions according to the invention, which integrate grafted polysaccharide-based hydrophilic polymers II, are particularly valuable in terms of bioadhesiveness, which makes them extremely advantageous for application, for example, to mucosae. Thus, for ocular application, it proves to be particularly advantageous for the hydrophilic polymers II present in the emulsion to be hyaluronic acids grafted with cyclodextrins.

Moreover, without wishing to be bound in any way to a particular theory, it appears to be possible to put forward that, insofar as the hydrophilic polymers II are polysaccharides bearing cyclodextrins, the structure of the droplets of the dispersed phase is, as a general rule, such that the external layer of the droplets essentially consists of polysaccharides. In any event, in particular when the polysaccharides are dextrans, the droplets generally have a tendency to adhere to the surface of certain mucosae, at which they subsequently deliver, generally gradually, the lipophilic compound that they contain. It is thus possible, by applying a composition according to the invention comprising a lipophilic compound with a therapeutic effect to a given mucosa (nasal mucosa, ocular mucosa, etc.), to carry out a selective administration of the compound at this mucosa. Moreover, it also appears to be possible to put forward that, during oral administration, the specific structure of the droplets promotes their translocation through the digestive epithelium, and the passing of the encapsulated lipophilic active ingredients into the blood network.

When the emulsions according to the invention are intended for vectorizing medicament-type compounds, it is generally advantageous for the polymers I and/or II to be substituted with groups that allow cell targeting. In this context, it may be advantageous, for example, for the polymers I and/or II to be complexed with ligands of folic acid type.

Moreover, in order to improve the "stealth" nature of the emulsions according to the invention (i.e. their ability to circulate for a sustained amount of time in the organism while at the same time avoiding detection by the immune system), it may be advantageous for the droplets forming the emulsions of the invention to have external groups of polyethylene glycol (PEG) type. To do this, macromolecules of polysaccharides (preferably fucoidans, heparin or hyaluronic acid), optionally bearing both cyclodextrins as defined above and PEG chains, can, for example, be used as polymer II.

Another embodiment of particles grafted with PEG groups consists in adding, to the associative system of the polymers I and/or II and of the lipophilic compound, compounds of PEG-[Alk] type, where Alk represents a C10 to C18, preferably C12 to C16, alkyl group, or else an adamantyl group. Where appropriate, the addition of the compounds of PEG-[Alk] type can be carried out before or after formation of the emulsion from the associative system (polymer I/II+lipophilic compound). Generally, it is preferred, however, for this addition to be carried out after formation of the particles.

Irrespective of the nature of the polymer I or II, the cyclodextrins forming the polymer (I) or present on the polymer (II) can be modified, i.e. some of their groups can have undergone a chemical conversion. For example, they may be cyclodextrins bearing sulfate, alkyl, hydroxyalkyl (e.g., hydroxyethyl, hydroxypropyl, dihydroxypropyl, hydroxybutyl or hydroxyisobutyl), carboxyalkyl (e.g. carboxymethyl), glycosyl and/or amino groups.

That being the case, given the presence of cyclodextrin units within their structure, the polymers I and II are particularly suitable for encapsulating chemical compounds, and most particularly for encapsulating chemical compounds having groups of hydrophobic nature. Thus, the polymers I and II according to the invention are capable of integrating, in encapsulated form, numerous types of neutral or charged chemical compounds. The compounds that may be capable of being encapsulated within these polymers comprise, in particular, compounds having hydrophobic groups, in particular alkyl groups, containing generally from 6 to 18 carbon atoms.

More specifically, the lipophilic compounds capable of being used in the emulsions according to the invention are all compounds capable of forming inclusion complexes with the cyclodextrin units comprised by the polymers I and II. For further details with regard to the formation of inclusion complexes between chemical compounds and cyclodextrins, and also regarding the nature of the compounds capable of forming such complexes, reference may in particular be made to "Cyclodextrins and their inclusion complexes", Szejtli J., Academia Kiado, Budapest, 1982 [26].

Generally, simply bringing the abovementioned lipophilic compounds into contact with a polymer I or II according to the invention is sufficient to encapsulate said lipophilic compounds with said polymers, in particular when said composition is essentially based on water and on the polymers I or II.

The lipophilic compound is generally a compound which has groups of hydrophobic nature, advantageously groups that are hydrocarbon chains containing from 8 to 18 carbon atoms, and preferably from 10 to 18 carbon atoms. Advantageously, this lipophilic compound is a compound capable of forming an inclusion complex with one of the cyclodextrin units comprised in the polymers I or II.

The lipophilic compound of the emulsions according to the invention can be a compound chosen from the group comprising:
fatty substances chosen from the group comprising natural oils of vegetable, animal or marine origin (such as olive oil, sesame oil, argan oil, palm oil, soybean oil, woad oil, turtle oil, babassu oil, aloe vera, avocado oil, allantoin, bisabol, grapeseed oil, apricot oil, wheatgerm oil, almond oil, arachis oil, macadamia nut oil, sea buckthorn oil, evening primrose oil, borage oil, ginger oil, geraniol, jujube oil, mink oil, lanolin), synthetic oils, mineral oils (such as isohexadecane, isoparaffin, ceresin, petrolatum), hydrogenated oils, silicone oil, hydrocarbon-based compounds (such as liquid paraffin, terpenes, squalene), saturated or unsaturated fatty acids (such as myristic acid), fatty acid esters, waxes (such as whale wax, beeswax, jojoba oil which is in fact a liquid wax), fatty alcohols (such as myristyl alcohol, cetyl alcohol, stearyl alcohol, myricyl alcohol), butters (such as shea butter or cacao butter), wax esters, or a mixture thereof,
lipophilic odorous compounds used in the manufacturing of fragrances, and
lipophilic active ingredients.

The fatty substances can be chosen from any fatty substances commonly used in the formulation of pharmaceutical, cosmetic and/or agri-food compositions. The examples mentioned above are merely an illustration of the fatty substances that can be used, and are in no way limiting.

The term "active ingredient", as used herein, refers to a molecule which has a therapeutic or cosmetic effect. For example, it may be any molecule having therapeutic properties that is part of the composition of a medicament. Mention may, for example, be made of nonsteroidal anti-inflammatory drugs (NSAIDs), abortion drugs, alpha-blockers, alpha2-agonists, aminosides, analgesics, anesthetics, local anesthetics, anorexigenics, 5HT3 antagonists, calcium antagonists, anti-angina agents, antiarhythmics, antibiotics, anticholinergics, anticholinesterase agents, antidiabetics, antidiarrhea agents, antidepressants, antihistamines, antihypertensives, antimycotics, antimalarias, antiparasitics, antipsychotics, antipyretics, antiretroviral agents, antiseptics, antispasmodics, antivirals, antiemetics, antiepileptics, anxiolytics, barbiturates, benzodiazepines, bronchodilators, beta-blockers, chemotherapeutic agents, corticosteroids, diuretics, loop diuretics, osmotic diuretics, depressants, glucocorticoids, hallucinogenics, hypnotics, immunosuppressants, carbonic anhydrase inhibitors, neuraminidase inhibitors, proton pump inhibitors, TNF inhibitors, selective serotonin reuptake inhibitors, HMG-CoA reductase inhibitors (or statins), keratolytics, laxatives, mineralocorticoids, muscle relaxants, neuroleptics, psychotropics, spasmolytics, stimulants, sedatives, tocolytics or vasodilators. This list is not exhaustive and extends to any therapeutic active ingredient known to those skilled in the art.

It may also be any molecule that is part of the composition of a cosmetic preparation which ensures the effectiveness of the product (as opposed to the other ingredients of the composition, such as the excipients or other additives (adjuvants (for fragrancing, foaming, etc.), preservatives, in particular parabens, coloring agents, antioxidants, emulsifiers, pH stabilizers, surfactants, viscosity-controlling agents, etc.), which perform a different function). The term "active ingredient" is commonly used in the cosmetics industry, even though the expression "active ingredient" is normally reserved for medicaments. In the present description, the term "active ingredient" is used to denote an active substance with a therapeutic or cosmetic effect. Thus, an active ingredient may be any molecule providing the cosmetic effect of cosmetic products such as hygiene products (makeup remover, toothpaste, deodorant, shower gel, intimate cleansing gel, soap, shampoo), care products (antiwrinkle cream, day cream, night cream, moisturizing cream, floral water, scrubbing product, milk, beauty mask, lip balm, tonic), hair products (conditioner, hair straightening product, gel, oil, lacquer, mask, dye), makeup products (dark eye circle concealer, artificial tanning product, eyeliner, rouge, foundation, khol, mascara, powder, skin whitening product, lipstick, nail varnish), fragrances (eau de cologne, eau de toilette, perfume), sun products (aftersun and sun creams, oils or lotions), shaving products and hair removal products (aftershave, hair removal cream, shaving foam), bath and shower preparations (bubble bath, bath oil, bath salts), to cite just a few. Cosmetics are hygiene and beautifying products. A cosmetic is a substance or a preparation intended to be brought into contact with various superficial parts of the human body, in particular the epidermis, the body hair and head hair systems, the external organs, the teeth and mucous membranes, with a view, exclusively or mainly, to cleansing them, protecting them, fragrancing them, maintaining the human body in good condition, modifying its appearance or correcting the odor thereof. Thus, the term "cosmetic effect" as used in the present description, refers to the abovementioned hygiene or beautifying effect that the cosmetic product is intended and designed to accomplish.

By way of cosmetic active ingredients, mention may, for example, be made of fruit acids (exfoliants), retinol or vitamin A (antioxidant), certain essential oils, hyaluronic acid (moisturizer), vegetable oils such as jojoba oil (*Simmondsia chinensis*) which is, incidentally, a light natural sunscreen, avocado (*Persea gratissima*) oil, almond (*Prunus duclis*) oil, olive (*Olea europaea*) oil, wheatgerm (*Triticum vulgare*) oil, arachis oil, macadamia (*Macadamia ternifolia*) nut oil, palm oil, sea buckthorn (*Hippophae rhamnoides*) oil, borage oil, evening primrose oil, grapeseed (*Vitis vinifera*) oil, cacao (*Theobroma cacao*) butter, shea (*Butyrospermum parkii*) butter, and moisturizing substances such as silk proteins (which are active substances originating from the cocoons of silk-producing worms), aloe vera, algae extracts, and amino acids (which are responsible for cell metabolism, fix water well and participate in the formation of the skin moisturizing agent (natural moisturizing factor or "NMF")). This list is not exhaustive and extends to any cosmetic active ingredient known to those skilled in the art.

The exact nature of the lipophilic compound can vary to quite a large extent. However, in particular insofar as the polymers I or II can be chosen from nontoxic and biocompatible compounds, and the presence of traces of organic solvents or of surfactants can be avoided, one of the main applications that can be envisioned for an emulsion according to the invention is the vectorizing of active ingredients, in particular compounds having a therapeutic or cosmetic effect. Thus, the present invention also relates to the use of an emulsion according to the invention for vectorizing lipophilic compounds having a therapeutic or cosmetic effect, or for agri-food use (e.g., fish oil).

Thus, according to one particularly advantageous embodiment, an emulsion according to the invention can comprise, as a lipophilic compound, at least one active compound as a medicament, this active lipophilic compound as a medicament preferably being capable of forming an inclusion complex with one of the cyclodextrin units comprised within the polymers I or II.

Such an emulsion according to the invention can generally be used as a pharmaceutical composition for administration by injection or via the oral route, or else by the dermal or subcutaneous route, via the nasal route, via the pulmonary route or via the ocular route, and, more broadly, for any administration at the mucosal level, or at the level of a specific site (tumor, lumen of certain blood vessels, etc.). In this context, it is most commonly preferred for the composition to consist essentially of water, of the polymers I and/or II and of the lipophilic compound, optionally in combination with one or more pharmacologically acceptable excipients suitable for the route of administration envisioned. However, broadly, a composition according to the invention can, in this type of application, take the form of any pharmaceutical formulation integrating an emulsion according to the invention where the lipophilic compound is an active ingredient as a medicament. In the case of a composition specifically intended for administration by intravenous injection, it is generally preferred for the droplets of the dispersed phase to have an average hydrodynamic diameter at most equal to 200 nm.

With regard to the compositions intended for administration by intramuscular injection, it is preferred for the droplets of the disperse phase to have an average hydrodynamic diameter of between 200 and 5000 nm, preferably less than 1000 nm.

For example, the lipophilic compound as an active ingredient can be chosen from the group comprising emollients, anti-infectives, anticancer agents, anti-inflammatories, antibacterial agents, antifungal agents, antivirals, antiseborrheic agents, antiacne agents, antiparasitics, opioids, keratolytics, antihistamines, anesthetics, wound healing agents, pigmentation modifiers, UV-filters, free radical scavengers, moisturizers, vitamins, enzymes, or else polypeptides.

Thus, as active lipophilic compounds as medicaments that can be used in the emulsions of the invention, mention may in particular be made of molsidomine, ketoconazole, gliclazide, dichlofenac, levonorgestrel, paclitaxel, hydrocortisone, pancratistatin, ketoprofen, diazepam, ibuprofen, nifedipine, testosterone, tamoxifen, furosemide, tolbutamide, chloramphenicol, benzodiazepine, naproxene, dexamethasone, diflunisal, anadamide, pilocarpine, daunorubicin, doxorubicin, diazepam and piroxicam.

Among the vitamins, mention may be made of vitamin A, vitamin E, vitamin D, vitamin F, beta-carotene and carotenes.

The compositions of the invention comprising an active lipophilic compound as medicament generally induce, following their administration, a gradual release of the lipophilic compound forming an inclusion complex with the cyclodextrins of the polymers I or II, in particular when said composition is administered to a patient intravenously. It is thus possible, by means of such a composition, to carry out prolonged release of the active lipophilic compound.

In this context, without wishing to be bound in any way to a particular theory, it appears to be possible to put forward that the release of the lipophilic compound takes place with a partition equilibrium between the droplets of the disperse phase and the external medium. Thus, it appears that the internal hydrophobic cavity of each cyclodextrin constitutes a site that potentially accepts the molecules of active ingredients or lipophilic fragments thereof. The greater the affinity of the active ingredient for the cyclodextrins, the more its release will be slowed down. Consequently, an active lipophilic compound as a medicament contained in a composition according to the invention is most commonly released preferentially at the cells or tissues where this compound is consumed, i.e., most commonly, there where it plays an actual therapeutic role.

Still with regard to the compositions of the invention comprising an active lipophilic compound as a medicament, it should be noted that said compositions can generally be administered as such orally.

In this case, they can make it possible to orally administer an active lipophilic compound which has an unpleasant taste or odor (the encapsulation is generally capable of masking this taste or this odor) or alternatively a lipophilic compound which is fragile and/or difficult to absorb orally, for instance a compound chosen from anti-inflammatories such as piroxicam, ibuprofen and ketoprofen, hypoglycemic agents such as gliclazide, contraceptive agents such as D-norgestrel, or else antifungal or antiparasitic compounds such as ketoconazole or albendazole.

According to another embodiment, the lipophilic compounds present within the emulsions according to the invention can also be cosmetic active agents, and the composition according to the invention can then be advantageously used as a cosmetic composition.

In this context, the lipophilic compounds can, for example, be odorous compounds, for example of terpene type, or else a mixture of such compounds (fragrances, essences, essential oils, etc.). In such a composition, the odorous compounds generally have a weaker irritant capacity than in the nonencapsulated state, and they are released in a delayed manner, thereby improving the persistence of the fragrance. In the same way, other types of cosmetic agents preferably having a hydrophobic nature can be immobilized as lipophilic compound within a composition according to the invention, and then gradually released. Thus, a composition according to the invention can, for example, allow the controlled release of antiperspirant or else antibacterial agents. In a composition according to the invention intended for cosmetic use, the lipophilic compound can also be a coloring agent which is irritant or has a certain toxicity, the encapsulation of which makes it possible to reduce the adverse effects.

According to one embodiment, the lipophilic compound can be an organic anti-UV agent capable of being used in sunscreens or a photoprotective system capable of filtering UV radiation.

According to the invention, the expression "photoprotective system capable of filtering UV radiation" or "UV-filter" is intended to denote, generally, any compound or any combination of compounds which, via certain mechanisms of adsorption and/or reflection and/or scattering of UV-A or UV-B radiation, makes it possible to prevent or limit the coming into contact of the radiation ray with a surface (skin, hair) to which this compound or these compounds is or are applied.

Photoprotective filtering agents are typically synthetic molecules which provide photochemical protection by selective absorption of certain photons. They absorb the energy from ultraviolet rays. There is no chemical filtering agent which is effective over the whole of the UV spectra. There are narrow absorption spectrum filtering agents which are UVB selective (for example, benzimidazoles, benzylidenecamphor, cinnamates, esters of para-aminobenzoic acid (PABA), and broad spectrum filtering agents which are effective in the UVA range (for example, benzophenones, dibenoylmethane derivatives). From the qualitative point of view, several filtering agents are normally combined in order to obtain the maximum spectral absorption. The concentration in the final product does not generally exceed 6-8%. From the quantitative point of view, the absorbance of each screening agent depends on its concentration.

Among the organic anti-UV agents that can be used according to the invention, mention may be made, for example, of benzophenone-3, benzophenone-4, benzophenone-8, bis-ethylhexyloxyphenol methoxyphenyl triazine, butyl methoxydibenzoylmethane, 2-ethoxyethyl p-methoxycinnamate, diethylaminohydroxybenzoylhexyl benzoate, drometrizole trisiloxane, ethylhexyl methoxycinnamate (octyl methoxycinnamate or "octinoxate"), ethylhexyl salicylate, ethylhexyl triazone, homomethyl salicylate, methyl anthranilate, 4-methylbenzylidene camphor, methylene bis-benzotriazolyl tetramethylbutylphenol, octyl cyanophenylcinnamate, para-aminobenzoic acid, phenylbenzimidazole sulfonic acid, benzylidene malonate polysiloxane, triethanolamine salicylate and terephthalylidene dicamphor sulfonic acid.

For example, the lipophilic compound may be an organic anti-UV agent, such as ethylhexyl methoxycinnamate (also referred to as "Parsol® MCX" in the present description), corresponding to the following structure:

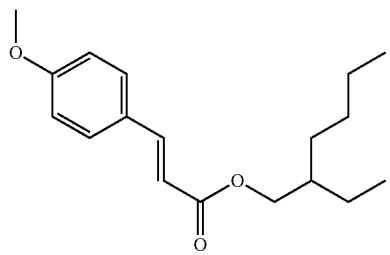 [SMILES: CCCCC(CC)COC(=O)/C=C/c1ccc(OC)cc1]

In this context, a subject of the present invention is based on the use of an emulsion as defined above, for the manufacture of cosmetic compositions for protecting the skin and/or the hair against ultraviolet radiation, in particular solar radiation. The invention also relates to a cosmetic treatment method for protecting the skin and/or the hair against ultraviolet radiation, in particular solar radiation, comprising the application, to the skin and/or the hair, of an effective amount of a composition comprising an emulsion as defined above.

More generally, the compositions of the invention can be used to carry out a gradual release of the lipophilic compounds in a medium into which they are introduced or else to limit the contacting of said lipophilic compounds with said medium, for example with a view to their protection, when they are molecules that are fragile with respect to the medium under consideration, or else to isolate compounds which may be pollutants (toxic, irritant, reactive, etc., agents) for this medium.

This general use of the compositions of the invention constitutes another subject of the present invention.

According to another aspect, the invention also relates to the compositions comprising an emulsion as defined above. Said composition can be for therapeutic, cosmetic or agrifood use, and can therefore further comprise, in addition to the emulsion according to the invention, any other component which is conventionally part of therapeutic, cosmetic or agrifood compositions.

According to another aspect, the invention also relates to a method for preparing an emulsion as described above. Thus, a method for preparing an emulsion as defined above is proposed, which is characterized in that it comprises:

(i) adding a lipophilic compound to an aqueous solution of a cyclodextrin unit-based polymer I or of a hydrophilic polymer II bearing cyclodextrins;
(ii) forming an emulsion of the mixture obtained in step (i).

The cyclodextrin unit-based polymer I or the hydrophilic polymer II bearing cyclodextrins is as defined above.

The lipophilic compound is as defined above.

As a general rule, the method of the present invention is extremely simple to carry out. Thus, step (i) of the method of the invention can consist of simple mixing, which is generally carried out at ambient temperature, i.e. most commonly between 15° C. and 30° C.

With regard to step (ii) of the method, it can be carried out by a means chosen from the group comprising sonication (preferably pulsed sonication), shear force homogenization (for example with an Ultra-Turrax®) and microfluidization (with a microfluidizer).

The operating principle of a homogenizer is the following: by virtue of the high speed of the rotor, the fluid to be processed is automatically drawn up in the axial direction into the dispersion head and subsequently compressed in the radial direction through the slits in the rotor/stator system. The material is thus subjected to very high shear and thrust forces. In addition, a high turbulence forms in the interstice between the rotor and the stator, giving rise to optimum mixing of the suspension.

Microfluidization makes it possible to physically reduce particles dispersed in a liquid or droplets to uniform submicrometric sizes. Microfluidization is a new type of process in the biotechnology, chemistry, pharmaceutical and food industries. Typically, the product to be processed enters the input tank; an amplifier, pneumatic or electrohydraulic pump, generating a virtually continuous pressure (up to 2755 bar), accelerates the flow to be treated to speeds reaching several hundred meters per second, propelling it into a processing zone called the interaction chamber. By virtue of the power of the shear and of the impacts in these microchannels, the particles or the droplets are reduced to sizes of less than one micron.

Advantageously, the formation of the emulsion in step (ii) can be carried out by pulsed sonication for a period of from 10 seconds to 15 minutes, preferably from 20 seconds to 5 minutes, preferably from 30 to 50 seconds. The formation of the emulsion in step (ii) can also be carried out by means of Ultra-Turrax® for a period of from 1 minute to 10 hours, preferably from 5 minutes to 5 hours, preferably from 10 minutes to 2 hours. The formation of the emulsion in step (ii) can also be carried out by passing a "coarse" emulsion (i.e. an emulsion containing large droplets obtained, for example, by vortexing) through a microfluidizer for a period of from 10 seconds to 5 minutes, preferably from 30 seconds to 3 minutes, preferably from 45 seconds to 2 minutes, advantageously about one minute.

In this regard, it should be clearly emphasized that the method of the invention does not require the use of solvents or surfactants. Consequently, a composition according to the invention is, generally, free of any trace of organic solvent and/or of surfactant. Thus, according to one embodiment, an emulsion according to the invention can comprise water, polymers I and/or II and a lipophilic compound, as defined above, to the exclusion of any other compound.

In certain embodiments, in step (i) of the method, the lipophilic compound is added as such when it is in liquid form. Alternatively, when the lipophilic compound is in solid form, said compound is added in solution in a water-immiscible lipid solvent, such as Miglyol®, isopropyl myristate or squalene; or else a liquid fatty substance chosen from the group comprising natural oils of vegetable, animal or marine origin (such as olive oil, sesame oil, argan oil, palm oil, soybean oil, woad oil, turtle oil, babassu oil, aloe vera, avocado oil, allantoin, bisabol, grapeseed oil, apricot oil, wheat-germ oil, almond oil, arachis oil, macadamia nut oil, sea buckthorn oil, evening primrose oil, borage oil, ginger oil, geraniol, jujube oil, mink oil, lanolin), synthetic oils, mineral oils (such as isohexadecane, isoparaffin, ceresin, petrolatum), hydrogenated oils, silicone oils, hydrocarbon-based oils (such as liquid paraffin, terpenes, squalene), saturated or unsaturated fatty acids (such as myristic acid), fatty acid esters, liquid waxes (such as jojoba oil), fatty alcohols (such as myristyl alcohol, cetyl alcohol, stearyl alcohol, myricyl alcohol) or a mixture thereof.

Advantageously, the concentration of the cyclodextrin unit-based polymer I or of the hydrophilic polymer II bearing cyclodextrins in the aqueous solution of step (i) is between 20 and 200 mg/ml, preferably between 25 and 175 mg/ml, preferably between 50 and 150 mg/ml, preferably between 90 and 110 mg/ml.

Advantageously, in step (i) the amount of lipophilic compound is between 1 and 500 mg/ml, preferably between 1 and 400 mg/ml, preferably between 1 and 200 mg/ml, preferably between 1 and 100 mg/ml, preferably between and 50 mg/ml, preferably between 1 and 25 mg/ml, preferably between 5 and 20 mg/ml, preferably between 5 and 15 mg/ml.

It is often advantageous for the (lipophilic compound)/(polymer I or II) weight ratio of the total weight of the lipophilic compounds relative to the total weight of the polymers I or II to be between 1% and 50%, this ratio preferably being greater than 2%, and advantageously greater than 3%.

The method according to the invention can further comprise a step of increasing the content of lipophilic compound of the emulsion. This step can be carried out by ultracentrifuging said emulsion. This step can be carried out by centrifuging an emulsion according to the invention at least 40 000 revolutions per minute (rpm) for a period of time ranging from 5 minutes to 1 hour and preferably to 15 minutes. Two phases are then observed: a first phase consisting of an aqueous solution of polymer I or polymer II, and a second phase consisting of a concentrated emulsion which is most common in the form of a cream. The average hydrodynamic diameter of the droplets of the resulting emulsion is much lower than that of the droplets of the emulsion before ultracentrifugation. On average, the average hydrodynamic diameter goes from about 0.8 mm before ultracentrifugation to 400 to 500 nm after ultracentrifugation. The stability of the emulsion thus ultracentrifuged is consequently increased.

Owing to their remarkable stability, the emulsions according to the invention can generally be subjected to a freeze-drying step.

Thus, the method according to the invention can further comprise a step of freeze-drying the emulsion. This step can be carried out using a commercial freeze drier. Where appropriate, this freeze-drying step can generally be carried out by abruptly cooling the composition (generally in liquid air or liquid nitrogen), and then subliming the water at very low pressure. The freeze-drying can be carried out using the normal freeze-drying parameters for aqueous mixtures or solutions. For example, the freeze-drying can be carried out under a vacuum of from 5 Pa to 30 Pa for a period of between 24 and 80 hours, preferably about 72 hours. At the end of the freeze-drying, a powder which is generally in the form of a compact powder with a cotton wool-like appearance is obtained, which can be stored for an indeterminate period of time at ambient temperature (i.e. between 15 and 25° C.) or with refrigeration. The emulsion thus freeze-dried can be subsequently reconstituted by dispersing the freeze-dried material in water. The amount of water used to redisperse the freeze-dried material can be a volume equivalent to that which would have been withdrawn during the freeze-drying step. As a general rule, the size of the droplets of the emulsion thus reconstituted is equivalent to that of the initial emulsion. Alternatively, the freeze-dried material may be redispersed in a smaller or larger volume, depending on whether a more or less concentrated emulsion, respectively, is desired.

The compositions obtained at the end of such a freeze-drying step, which can be dispersed in water so as to result in the reconstitution of an emulsion according to the invention, constitute another particular subject of the present invention. Thus, according to another aspect, the invention relates to a composition obtainable by freeze-drying an emulsion as defined above.

According to yet another aspect, the invention relates to an emulsion obtainable by a method as defined above. The invention also relates to the use of such an emulsion for the manufacture of a cosmetic, pharmaceutical or agri-food composition.

According to yet another aspect, the invention relates to the use of an emulsion obtainable by a method as defined above, for carrying out a concentrated encapsulation of lipophilic compounds. Indeed, as described above, the inventors have discovered that it is possible to increase the content of lipophilic compound in the emulsion according to the invention by ultracentrifugation. This aspect is of use in the cosmetics field, in particular in the fragrance field. The method according to the invention in fact makes it possible to incorporate a large amount of a high concentration of odorous lipophilic compound (e.g., fragrance) into a composition according to the invention. In addition, the latter point applies to all the other active ingredients or lipophilic compounds capable of being encapsulated in cyclodextrins.

According to yet another aspect, the invention relates to the use of an emulsion obtainable by a method as defined above, for masking the odor and/or the taste of a lipophilic compound of a cosmetic, pharmaceutical or agri-food composition.

According to yet another aspect, the invention relates to the use of an emulsion obtainable by a method as defined above, for the controlled release of a lipophilic active ingredient.

According to yet another aspect, the invention relates to use of an emulsion obtainable by a method as defined above, for prolonging the cosmetic or therapeutic effect of a compound of a cosmetic or pharmaceutical composition. It may, for example, be the effect of a deodorant, the repellant effect of a mosquito repellant, etc.

According to yet another aspect, the invention relates to the use of an emulsion obtainable by a method as defined above, for:
  toning down or masking the odor of a lipophilic compound contained in said emulsion,
  toning down or masking the unpleasant taste of a lipophilic compound contained in said emulsion,
  improving the stability of readily oxidizable lipophilic compounds,
  improving the stability of readily volatile lipophilic compounds, and/or
  increasing the solubility of insoluble lipophilic compounds.

According to yet another aspect, the invention relates to the use of a non-covalent and non-crystalline inclusion complex made up (i) of a cyclodextrin unit-based polymer or of a hydrophilic polymer bearing cyclodextrins and (ii) of a lipophilic compound, for stabilizing an emulsion, the cyclodextrin unit-based polymer, the hydrophilic polymer bearing cyclodextrins and the lipophilic compound being as defined above.

Thus, according to the method of the invention, it is possible to prepare extremely stable, simple or multiple, oil-in-water or water-in-oil emulsions very simply and with a low input of energy.

The stability of the emulsions according to the invention can in particular be demonstrated by the preservation of the average hydrodynamic diameter of the droplets of the dispersed phase following storage. Thus, in general, following storage for 24 hours, the average hydrodynamic diameter of the droplets of an emulsion according to the invention remains less than or equal to 5000 nm. Most commonly, following storage for 24 hours, the average hydrodynamic diameter of the droplets of an emulsion according to the invention remains less than or equal to 800 nm, preferably less than or equal to 500 nm, advantageously less than or equal to 400 nm, and even more advantageously less than Or equal to 300 nm. Preferably, the average hydrodynamic diameter of the droplets of an emulsion according to the invention remains less than or equal to 500 nm, and preferably less than or equal to 400 nm, following storage for 2 days, or even following storage for 5 days, or even following storage for 15 days, or even following storage for 25 days, and even, in certain cases, after storage for 60 days. It should, however, be emphasized that, in order to observe good preservation of the average hydrodynamic diameter of the droplets following prolonged storage, it may sometimes be necessary to store the emulsion in a nonoxidizing atmosphere (under argon, for example) so as to prevent aging of its constituents, which is capable of calling into question the stability of the system.

The term "average hydrodynamic diameter", in the sense that it is used in the present description, denotes the size of a droplet of oil in an aqueous medium (oil-in-water emulsions) or of a droplet of water in an oily medium (water-in-oil emulsions), which takes into account the average diameter of the droplet in its conformation in an aqueous or oily medium, and also its possible solvation layer. The average hydrodynamic diameter of a population of droplets in an aqueous or oily medium can in particular be determined by quasi-elastic light scattering within the medium under consideration, in particular using an apparatus of Nanosizer type. This type of apparatus also makes it possible to determine, for the population of droplets, a polydispersity index of the hydrodynamic diameter, which reflects the distribution of the hydrodynamic diameters, which is more or less narrow around the average value.

In certain embodiments, the emulsion according to the present application does not contain cyclodextrin compounds other than the cyclodextrin unit-based polymer I or the hydrophilic polymer II bearing cyclodextrins as defined in the present document, this being able to apply independently to each of the embodiments moreover described in the present document. For example, the emulsion according to the invention does not contain cyclodextrin monomers, for example hydroxyalkylated cyclodextrins such as those described in document JP 03/058906. For example, the emulsion according to the present invention also does not contain cyclodextrin oligomers, i.e. compounds containing 2 to 6 or even 3 to 4 cyclodextrins that are crosslinked or connected to one another, optionally via a spacer group (linker), such as the beta-cyclodextrin trimers or tetramers described in document JP 61/227,517.

Thus, according to certain embodiments, an emulsion according to the invention can comprise water, polymers I and/or II and a lipophilic compound, as defined above, with the exclusion of cyclodextrin monomers or oligomers as defined in the previous paragraph.

Other features, aspects and advantages of the present invention will emerge on reading the illustrative examples set out hereinafter and the appended figures.

EXAMPLES

Comparative Example 1

"Emulsions" from Cyclodextrin Monomers

Compared with the work already reported in the literature [1-8], it is observed that the addition of the cyclodextrin monomers to double (multiple) emulsions leads to considerable stabilization of the system. On the basis of these observations, several tests with these three monomers (α-, β- and γ-cyclodextrins) were carried out in order to increase the stability of emulsions based on a Parsol® MCX oil (anti-UV filtering agent).

Figure 1:
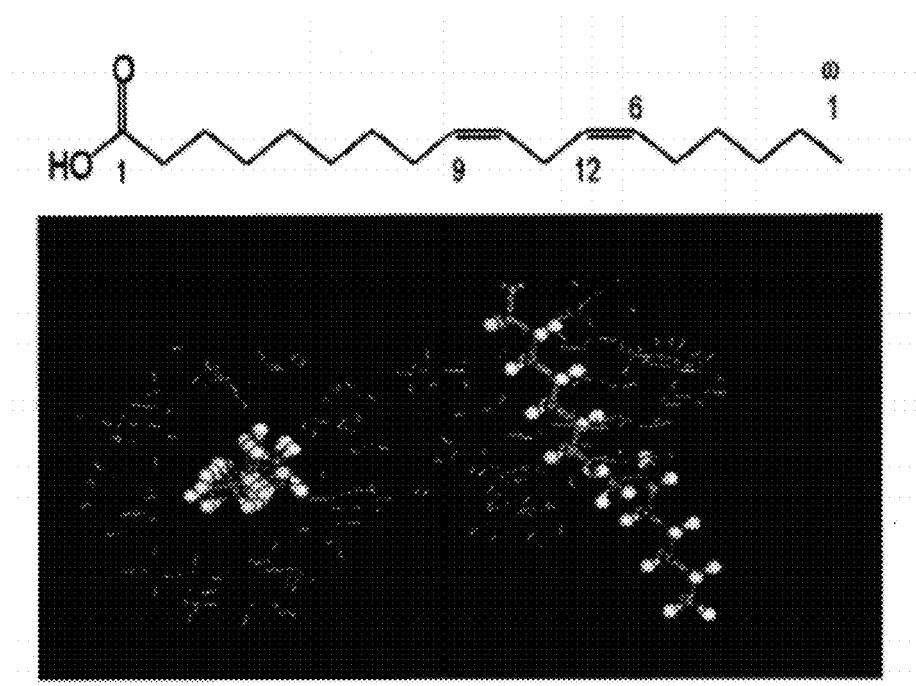
FIG. 1 represents a molecular modeling of the Parsol® MCX/β-cyclodextrin dimer system.

Firstly, a molecular modeling study preliminary to the experimental part was carried out. It was thus observed (FIG. 1), with a cyclodextrin dimer, that an interaction was possible with two Parsol® MCX molecules.

Attempts to prepare emulsions were carried out in three steps as follows:
(1) solubilization of the β-cyclodextrin (β-CD) (17 mg/ml) in water (limiting factor: the solubility of the β-CD);
(2) addition of the oil (Parsol® MCX) (10 μl for 1 ml of aqueous solution of β-cyclodextrin);
(3) sonication in an ice-cold bath (40 sec, pulsed).

Briefly, the following protocol was used:

The α-, β- or γ-cyclodextrin monomers are placed in solution in water at a concentration of 17 mg/ml. 10 mg of Parsol® MCX are added to 1 ml of the aqueous solution of α-, β- or γ-cyclodextrin thus prepared. The mixture is then subjected to pulsed sonication for 40 seconds in an ice-cold bath (0° C.). The resulting product is stored at 25° C. with tangential agitation.

Figure 2:
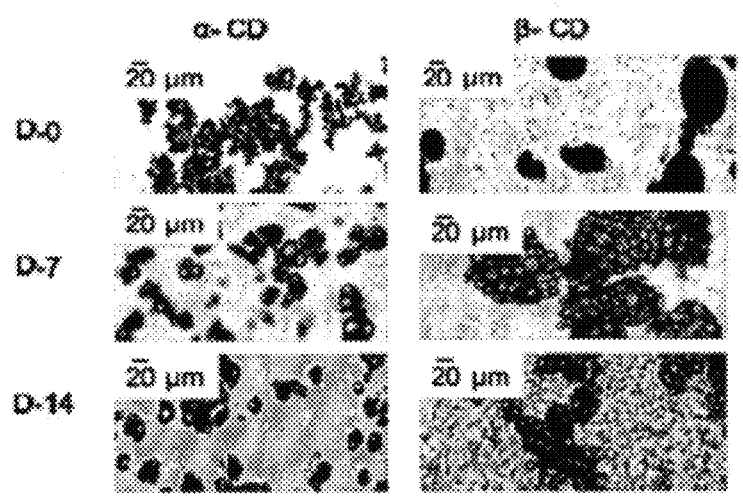
FIG. 2 represents optical microscopy images of an insoluble precipitate obtained after emulsion of an aqueous solution of α-cyclodextrin (α-CD) and Parsol® MCX or an aqueous solution of β-cyclodextrin (β-CD) and Parsol® MCX, on the day of preparation of the emulsions (D-0) and seven and fourteen days later (D-7 and D-14 respectively).
Figure 3A:
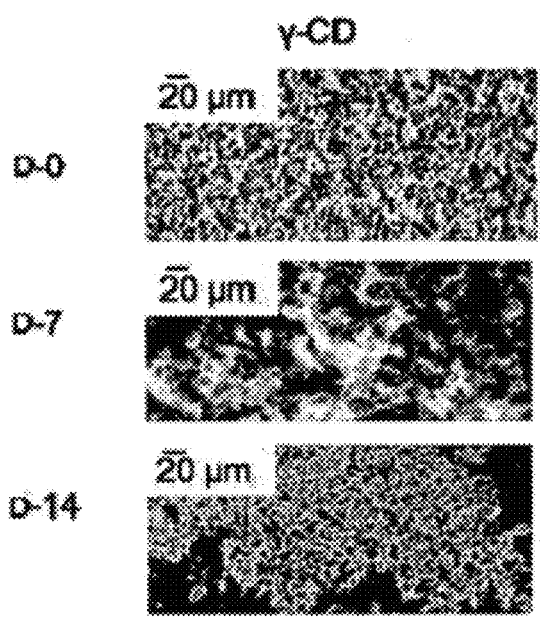
FIG. 3A represents optical microscopy images of an oil-in-water emulsion obtained from an aqueous solution of γ-cyclodextrins (γ-CD) and Parsol® MCX, on the day of preparation of the emulsion (D-0), and also an insoluble precipitate obtained seven and fourteen days after the preparation of the abovementioned emulsion (D-7 and D-14 respectively).

However, the attempts to prepare emulsions from the (α-, β-) cyclodextrin monomers result in the formation of an insoluble precipitate (FIG. 2). The γ-cyclodextrins result firstly in the formation of an emulsion (for two days) and then a precipitation (FIG. 3A).

Other products were tested in the same way (with the α- and β-monomers), such as geraniol, ginger oil or a fragrance concentrate. Thus, attempts to prepare emulsions from the following components were carried out, using the same protocol as that described for Parsol® MCX above:

(a) aqueous solution of α-cyclodextrins and geraniol,
(b) aqueous solution of α-cyclodextrins and a fragrance concentrate,
(c) aqueous solution of α-cyclodextrins and ginger oil,
(d) aqueous solution of β-cyclodextrins and geraniol,
(e) aqueous solution of β-cyclodextrins and a fragrance concentrate or
(f) aqueous solution of β-cyclodextrins and ginger oil.

Figure 3B:
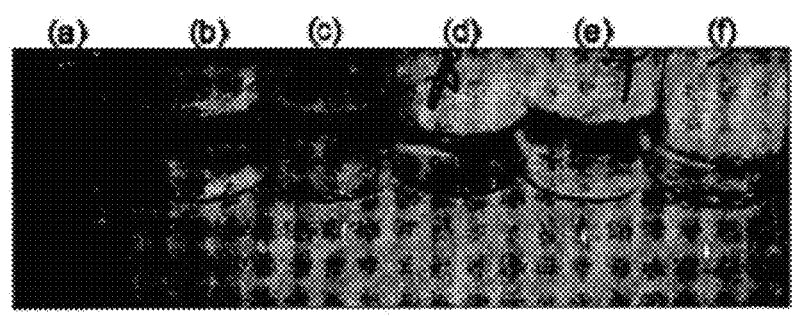
FIG. 3B represents a photograph of the samples exhibiting an insoluble precipitate obtained after the preparation of an emulsion from: (a) an aqueous solution of α-cyclodextrins and geraniol, (b) an aqueous solution of α-cyclodextrins and a fragrance concentrate, (c) an aqueous solution of α-cyclodextrins and ginger oil, (d) an aqueous solution of β-cyclodextrins and geraniol, (e) an aqueous solution of β-cyclodextrins and a fragrance concentrate or (f) an aqueous solution of β-cyclodextrins and ginger oil.

However, in all cases, the formation of an insoluble precipitate was observed very rapidly (from the first day) (FIG. 3B).

The cyclodextrin monomers do not therefore make it possible to form emulsions. Precipitates and not emulsions are obtained.

Comparative Example 2

"Emulsions" from Cyclodextrin Oligomers

To follow up on this not very encouraging result with the use of cyclodextrins (formation of a precipitate), tests were carried out with the following series of dimers/trimers (D/T) (% by weight of cyclodextrins in the polymer determined by NMR=50% by weight relative to the total weight of the oligomer) from CycloLab Cyclodextrin Research & Development Laboratory, Ltd. Budapest, Hungary:
(D, T) anionic α-cyclodextrin,
(D, T) sulfated α-cyclodextrin,
(D, T) γ-cylodextrin,
(D, T) anionic β-cyclodextrin,
(D, T) β-cyclodextrin,
(D, T) anionic γ-cyclodextrin,
(D, T) sulfated β-cyclodextrin,
(D, T) α-cyclodextrin.

The following protocol was used to prepare the various emulsions/precipitates:

The α-, β- or γ-cyclodextrin dimers/trimers are put into solution in water. 10 mg of Parsol® MCX are added to 1 ml of the aqueous solution of α-, β- or γ-cyclodextrin dimer/trimer thus prepared. The mixture is then subjected to pulsed sonication for 40 seconds in an ice-cold bath (0° C.). The resulting product is stored at 25° C. with tangential agitation.

The optical microscopy observation indicates, in all cases, the formation of an emulsion with an inhomogeneous size, of very variable (very large) droplets, but rapid coalescence after three-four days.

The cyclodextrin oligomers do not therefore make it possible to form stable emulsions.

In view of these results, it appears to be important to underline the influence of the molecular weight and of the size of the cavity of the cyclodextrin units, on the stability of the emulsions. As shown in comparative example 1 above, regarding the α-monomers (molecular weight=972 g/mol with an internal cavity diameter of 4.7-5.2 (Å)) and β-monomers (molecular weight=1135 g/mol with an internal cavity diameter of 6.0-6.4 (Å)), an insoluble precipitate is formed as early as the first day (day zero). However, the γ-monomer (molecular weight=1297 g/mol with an internal cavity diameter of 7.5-8.3 (Å)) initially forms an emulsion and then precipitates rapidly (two days). The tests carried out with the α-, β- and γ-cyclodextrin-based dimers/trimers in comparative example 2 indicate the formation of emulsions without precipitation, but with rapid coalescence. Thus, the molecular weight and the internal cavity size of the various cyclodextrins used (monomers, dimers/trimers) appear to have an effect on the stability of the emulsions, without, however, producing a viable stability for cosmetic, pharmaceutical and/or agri-food applications.

Examples Relating to Polycyclodextrin-Based Emulsions

Tests were carried out with high-molecular-weight cyclodextrin polymers ($10^5$ and $10^6$ g/mol).

Example 1

Synthesis of β-Cyclodextrin Unit-Based Polymers

Cyclodextrin unit-based polymers were prepared by reacting β-cyclodextrin (denoted β-CD) with epichlorohydrin in a basic medium, according to the procedure described in European Polymer Journal, vol. 33, no. 1, pp 49-57 (1997). The molar mass of the polymer can be modulated by varying the amount of epichlorohydrin used for the polycondensation.

1.1—Synthesis of a Poly-β-Cylodextrin Having a Molar Mass of 40 000 g/mol

In a two-necked flask, 5 g of β-CD were dissolved in an aqueous solution of sodium hydroxide at 33% by weight. This mixture was left to stir, at ambient temperature (20° C.), for 24 h, so as to deprotonate the hydroxyl groups.

2.7 ml of epichlorohydrin were subsequently introduced into the medium (β-CD/epichlorohydrin molar ratio=1/7), and the mixture was stirred vigorously and brought to 30° C. The medium was left under these conditions for 3 hours.

The reaction was then stopped, by adding acetone, which dissolves the excess epichlorohydrin. The supernatant acetone solution was then removed.

The polymer (precipitate) is dissolved in distilled water and the solution was brought to pH 12, and was stirred for 24 h. The pH value was then brought back to 7 (by adding 6N hydrochloric acid), and then the mixture was ultrafiltered with a membrane having a cut-off threshold of 1000 Daltons, in order to remove the salts.

The polymer obtained following these various steps was subsequently freeze-dried and then stored in a freezer. The molecular weight of 40 000 g/mol was determined by SEC chromatography, with pullulan calibration. The average number of β-CD units per polymer, calculated from this molecular weight, is 20.

1.2—Synthesis of a Poly-β-Cyclodextrin Having a Molar Mass of 2 600 000 g/mol

As for the polymer prepared in point 1.2 above, 5 g of β-CD were dissolved in an aqueous solution of sodium hydroxide at 33% by weight, in a two-necked flask. This mixture was left to stir at ambient temperature (20° C.), for 24 h, so as to deprotonate the hydroxyl groups.

3.8 ml of epichlorohydrin were then added to the medium (β-CD/epichlorohydrin molar ratio=1/10), and the mixture was stirred vigorously and brought to 30° C. The medium was left to evolve until the reaction medium was close to the point of gelling, i.e. until a medium of high viscosity was obtained.

The reaction was then stopped, by adding acetone, which dissolves the excess epichlorohydrin. The supernatant acetone solution was then removed.

The polymer (precipitated) is dissolved in distilled water and the solution was brought to pH12, and was stirred for 24 h. The pH value was then brought back to 7 (by adding 6N hydrochloric acid), and then the mixture was ultrafiltered with a membrane having a cut-off threshold of 1000 Daltons, in order to remove the salts. A second ultrafiltration was then carried out with a membrane having a cut-off threshold of 100 000 Daltons so as to remove the fractions of low molar mass.

The polymer obtained following these various steps was subsequently freeze-dried and then stored in a freezer. The molecular weight of 2 600 000 g/mol was determined by SEC chromatography, with pullulan calibration. The average number of β-CD units per polymer, calculated from this molecular weight, is 1350.

It is understood that the poly-α- and poly-γ-cyclodextrins could be obtained by means of similar protocols, replacing the β-CD with α-CD or γ-CD.

In the present document, the abbreviation "CD" refers to cyclodextrin. Thus, α-CD, β-CD and γ-CD signify monomers of α-cyclodextrin, β-cyclodextrin and γ-cyclodextrin, respectively. Likewise, poly-α-CD, poly-β-CD and poly-γ-CD signify polymers of α-cyclodextrin, β-cyclodextrin and γ-cyclodextrin, respectively.

Example 2

Preparation of Sunscreen Emulsions (Formulations) (Parsol® MCX) Via the Direct Route (Oil-in-Water) According to the Method of the Present Invention Direct-route emulsions corresponding to a total amount equal to 2 ml were prepared using β-cyclodextrin-based polymers with various molar mass values ($10^5$ and $10^6$ g/mol).

The cyclodextrin polymers are solubilized in water in a proportion of 100 mg/ml (the protocol can be adapted by varying the polycyclodextrin concentration between 20 mg/ml and 200 mg/ml).

A variable amount of the anti-UV agent (Parsol® MCX) is added to 2 ml of the cyclodextrin polymer solution in a proportion of 10 mg of Parsol® MCX per ml of polycyclodextrin solution (the protocol can be adapted by varying the Parsol® MCX concentration between 2.5 mg and 500 mg per ml of polycyclodextrin solution).

The emulsion is formed by pulsed sonication for a period of 40 seconds or using an Ultra-Turrax® for a varying period ranging from a few minutes up to two hours.

The resulting emulsions are conditioned for storage at 25° C., with tangential agitation, at 37° C. or 4° C. for a varying period ranging from a few days up to a few months before use.

Generally, a homogeneous fluid emulsion which is white in color and which is stable in a β-CD/Parsol® MCX molar ratio of 1/2.5, 1/1 and 1/0.5 is thus obtained.

Figure 9:
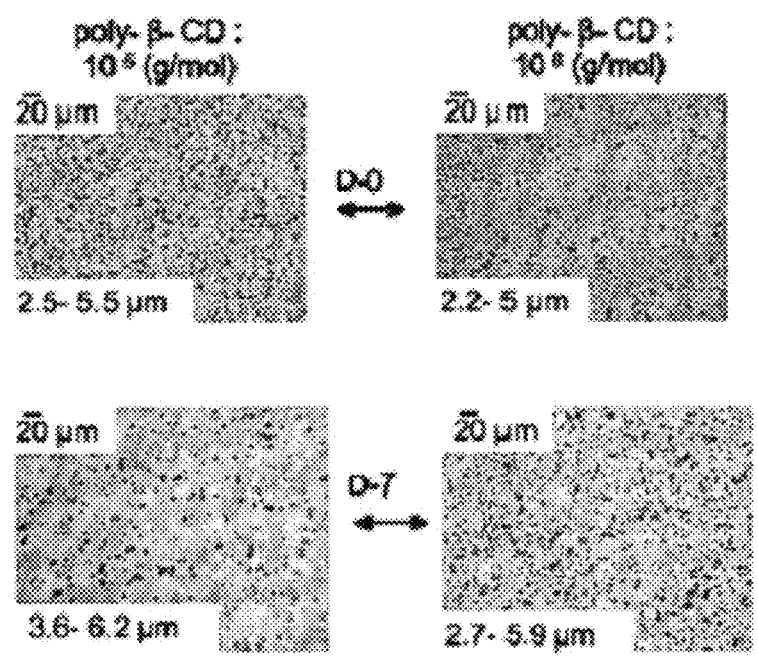
FIG. 9 represents a comparison between optical microscopy images of oil-in-water emulsions obtained from an aqueous solution of 100 mg/ml of β-cyclodextrin polymers (poly-β-CD) having a molar mass of $10^5$ and $10^6$ g/mol, and 10 μg/ml of Parsol® MCX, on day (D-0) and seven days (D-7) after preparation of the emulsions.

Examination under an optical microscope (observation of morphology and image analysis) and using dynamic light scattering techniques (DLS, laser particle sizing) show that the emulsions thus prepared form very well defined, spherical droplets with a size <10 μm (FIG. 9).

The particle size distribution of the resulting emulsion is stable over time, exhibiting no coalescence phenomenon.

One parameter studied was the polymer concentration. Several tests were carried out at varying concentrations in order to obtain emulsions with a droplet size stable over time. Overall, increasing the β-cyclodextrin polymer concentration in the system from 20 mg/ml up to 200 mg/ml and preferably 100 mg/ml makes it possible to obtain an emulsion that is stable over time.

Rheological studies on two systems containing 50 and 100 mg/ml of poly-β-cyclodextrins and 10 mg/ml of Parsol® MCX confirm the hypothesis that the amount of polymer used is an important parameter. However, a high surface tension value of about 60 mN/m was recorded for the system containing 50 mg/ml of poly-β-cyclodextrin, and a lower value, of about 13 mN/m, was recorded for the system containing 100 mg/ml of poly-β-cyclodextrin. This indicates the high stability of the emulsions containing more polymer (poly-β-cyclodextrin). Indeed, an increase in emulsion stability over time is observed with an increase in the amount of polymer in the emulsifying systems.

Figure 4:
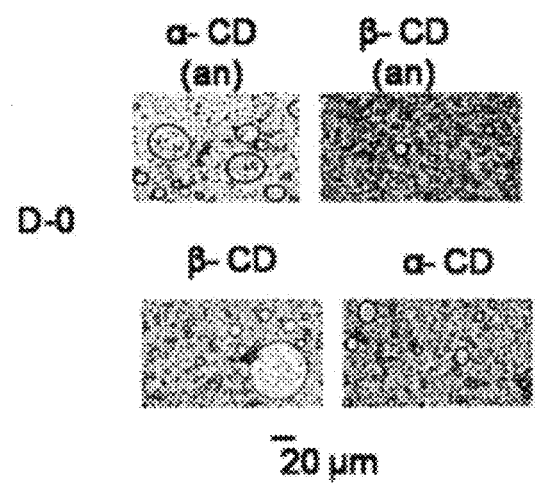
FIG. 4 represents optical microscopy images of oil-in-water emulsions obtained from an aqueous solution of α-, β-, γ-cyclodextrin (α-, β-, γ-CD) dimers/trimers and Parsol® MCX, on the day of preparation of the emulsions (D-0). "an" signifies anionic.
Figure 5:
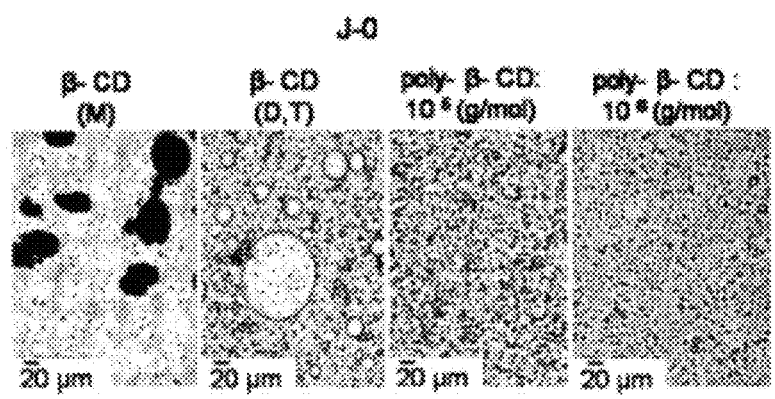
FIG. 5 represents optical microscopy images of the precipitates and of the oil-in-water emulsions obtained from an aqueous solution of β-cyclodextrin (β-CD) monomers (M), dimers (D), trimers (T) or polymers (poly) and Parsol® MCX, on the day of preparation of the emulsions (D-0).
Figure 6A:
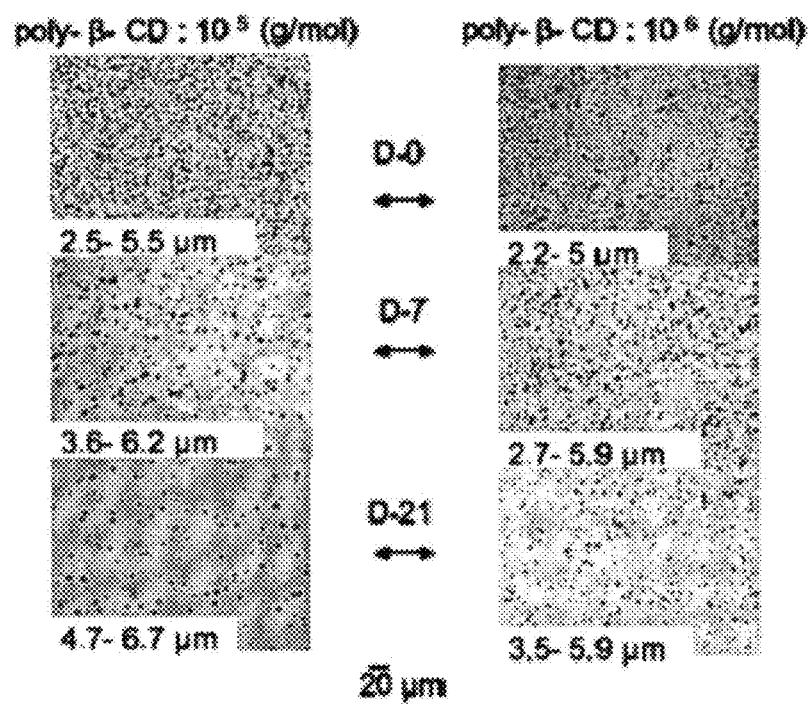
FIG. 6A represents optical microscopy images of oil-in-water emulsions obtained from an aqueous solution of β-cyclodextrin polymers (poly-β-CD) having an average molar mass of $10^5$ and $10^6$ g/mol, and Parsol® MCX, on the day of preparation of the emulsions (D-0), seven days after preparation (D-7) and twenty-one days after preparation (D-21). The average hydrodynamic diameters of the droplets are indicated on the images.
Figure 6B:
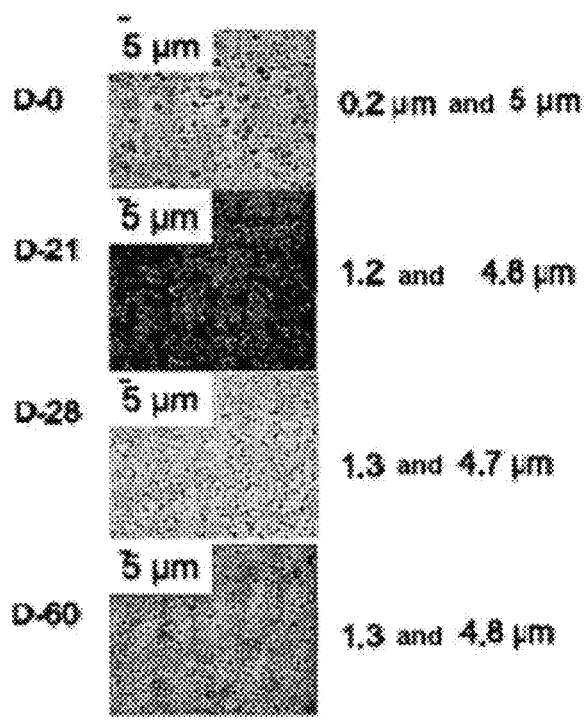
FIG. 6B represents optical microscopy images of oil-in-water emulsions obtained from an aqueous solution of β-cyclodextrin polymers (poly-β-CD) at 100 g/ml and borage oil, on the day of preparation of the emulsions (D-0) and twenty-one, twenty-eight and sixty days after preparation (D-21, D-28, D-60, respectively). The average hydrodynamic diameters of the droplets are indicated opposite the images. The emulsions are obtained by solubilizing a β-cyclodextrin polymer having an average molar mass of $10^5$ g/mol in water at a concentration of 100 mg/ml. 20 mg of borage oil are added to 2 ml of the aqueous solution of poly-β-cyclodextrin thus prepared. The mixture is then subjected to pulsed sonication for 40 seconds. The resulting emulsion is stored at 25° C. with tangential agitation. This result illustrates the remarkable stability of the borage oil emulsion over time (60 days).
Figure 6C:
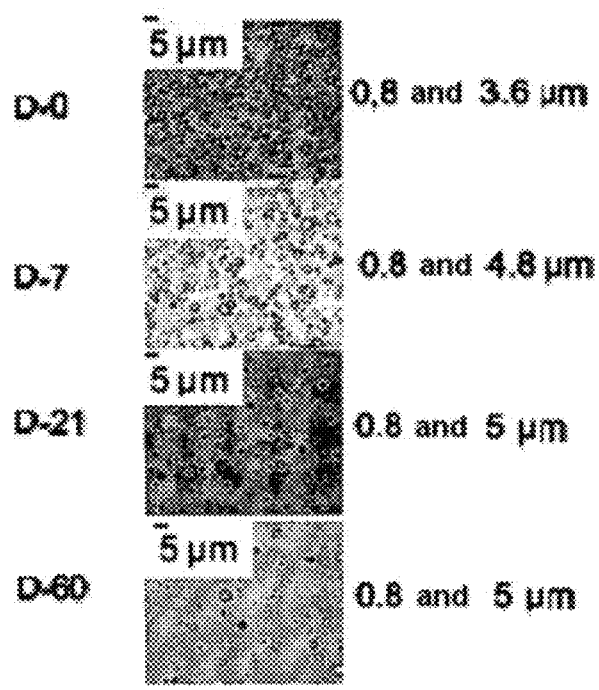
FIG. 6C represents optical microscopy images of oil-in-water emulsions obtained from an aqueous solution of β-cyclodextrin polymers (poly-β-CD) at 100 mg/ml and ginger oil, on the day of preparation of the emulsions (D-0) and seven, twenty-one and sixty days after preparation (D-7, D-21, D-60, respectively). The average hydrodynamic diameters of the droplets are indicated opposite the images. The emulsions are obtained by solubilizing a β-cyclodextrin polymer having an average molar mass of $10^5$ g/mol in water at a concentration of 100 mg/ml. 20 mg of ginger oil are added to 2 ml of the aqueous solution of poly-β-cyclodextrin thus prepared. The mixture is then subjected to pulsed sonication for 40 seconds. The resulting emulsion is stored at 25° C. with tangential agitation. This result illustrates the remarkable stability of the ginger oil emulsion over time (60 days).
Figure 6D:
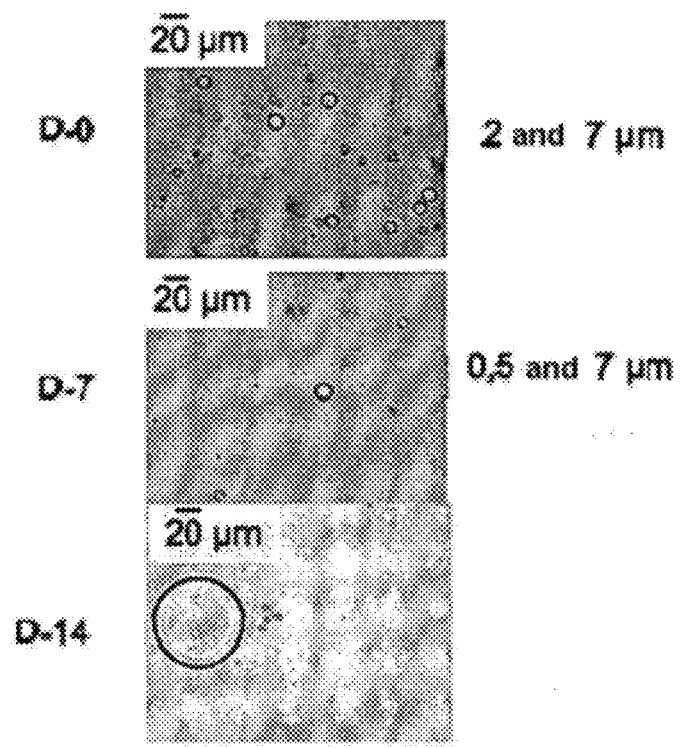
FIG. 6D represents optical microscopy images of oil-in-water emulsions obtained from an aqueous solution of γ-cyclodextrin polymers (poly-γ-CD) having an average molar mass of $2\times10^6$ g/mol at a concentration of 100 mg/ml and ginger oil, on the day of preparation of the emulsions (D-0) and seven and fourteen days after preparation (D-7, D-14, respectively). The average hydrodynamic diameters of the droplets are indicated opposite the images. The emulsions are obtained by solubilizing a γ-cyclodextrin polymer having an average molar mass of $2\times10^6$ g/mol in water at a concentration of 100 mg/ml. 20 mg of ginger oil are added to 2 ml of the aqueous solution of poly-γ-cyclodextrin thus prepared. The mixture is then subjected to pulsed sonication for 40 seconds. The resulting emulsion is stored at 25° C. with tangential agitation. This result illustrates the instability of the emulsion obtained with the γ-cyclodextrin polymer owing to the fact that the cavity diameter is too big (the inclusion complex formed with the lipophilic active ingredient (ginger oil) is not stable).

Thus, for tests carried out with 100 mg/ml of polymer (the system most stable over time), the presence of droplets of constant size and a morphology that is stable over time are observed by optical microscopy and dynamic light scattering (DLS) analysis (FIGS. 4, 5 and 6).

Figure 7:
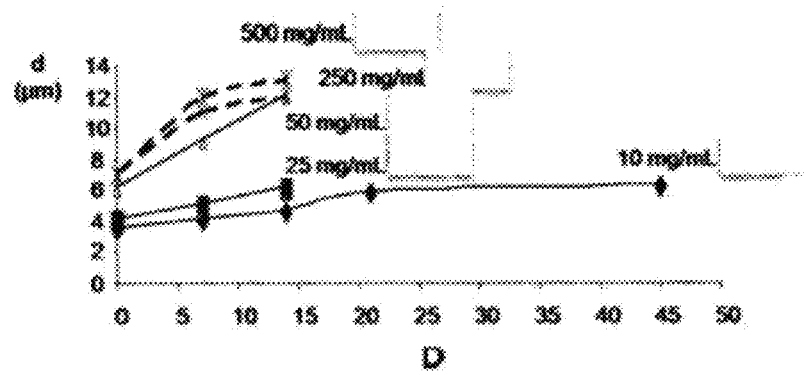
FIG. 7 represents the variation over time in the size of the droplets of emulsions prepared from an aqueous solution of 100 mg/ml of poly-β-cyclodextrin and Parsol® MCX, as a function of the Parsol® MCX concentration. Along the x-axis, "D" represents the number of days. Along the y-axis, "d" represents the average hydrodynamic diameter of the droplets in μm. The Parsol® MCX concentration is expressed in mg/ml.
Figure 8:
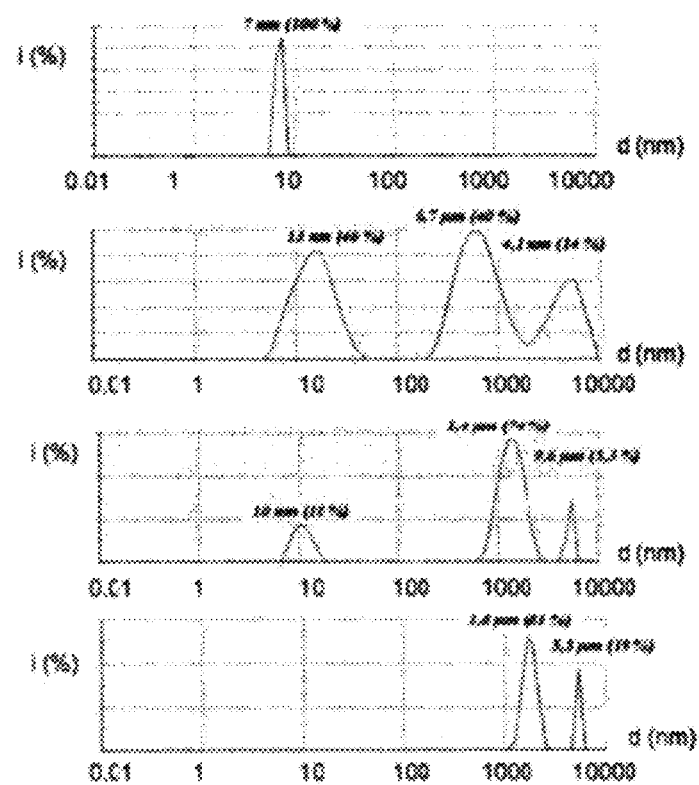
FIG. 8 represents the results obtained by dynamic light scattering (DLS) on poly-β-cyclodextrin systems, and Parsol® MCX droplets stabilized with poly-β-cyclodextrins, with in:
(a): pure poly-β-cyclodextrins at 100 mg/ml;
(b): poly-β-cyclodextrins at 100 mg/ml and Parsol®MCX at 2 mg/ml;
(c): poly-β-cyclodextrins at 100 mg/ml and Parsol®MCX at 5 mg/ml;
(d): poly-β-cyclodextrins at 100 mg/ml and Parsol® MCX at 10 mg/ml;
wherein, along the x-axis, "d" represents the diameter in nanometers (nm), and along the y-axis, "i" represents the intensity as a percentage.

Another important parameter studied was the cyclodextrin/Parsol® MCX ratio, with a variation in the concentration of Parsol® MCX (FIG. 7). In this case, a small increase in droplet size up to 12 μm is observed for a Parsol® MCX concentration of 500 mg/ml. Regarding this system, the presence of a supernatant oil drop is observed from the first day for the very high Parsol® MCX concentrations of 250 and 500 mg/ml. However, for 50 mg/ml of Parsol® MCX (50), no oil drop is visible at the emulsion surface, which indicates total incorporation of the oil (Parsol® MCX). Moreover, the analysis by dynamic light scattering (DLS) on a poly-beta-cyclodextrin solution demonstrates the presence of a particle size population with a very small diameter of about 7 (nm). This makes it possible to envision the stabilization of a large oil drop by several small particles of poly-beta-cyclodextrins.

Example 3

Preparation of Cosmetic Emulsions (Formulations) (Essential Oils, Fragrances, Mosquito Repellants) Via the Direct Route (Oil-in-Water) According to the Method of the Present Invention The emulsions containing essential oils or fragrances are prepared according to a protocol similar to that of example 2. The following oils and fragrances were used in an amount equal to 10 mg for a total volume of 2 ml of emulsion and for a concentration of β-cyclodextrin polymers equal to 100 mg/ml:
  lavandin essential oil,
  borage oil,
  ginger oil,
  geraniol,
  fragrance concentrate.

For each lipophilic compound, the emulsion is prepared by sonication for 40 seconds or using an ultra-turrax for 2 h, until a homogeneous emulsion is obtained. An emulsion which is stable is thus obtained.

Figure 10:
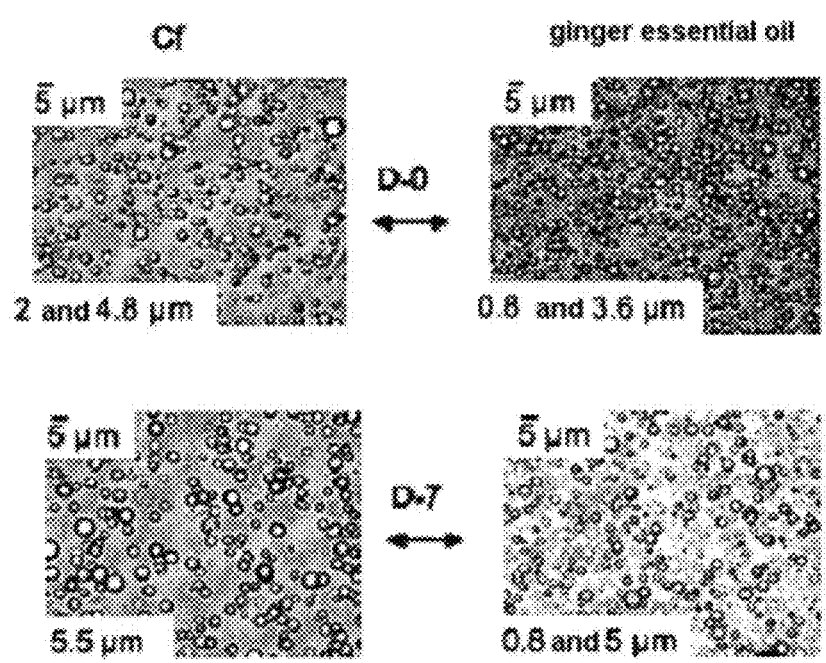
FIG. 10 represents a comparison between optical microscopy images of the oil-in-water emulsions obtained from an aqueous solution of 100 mg/ml of β-cyclodextrin polymers (poly-β-CD) and 10 μl/ml of fragrance concentrate or of ginger essential oil, on day (D-0) and seven days (D-7) after preparation of the emulsions.
Figure 11:
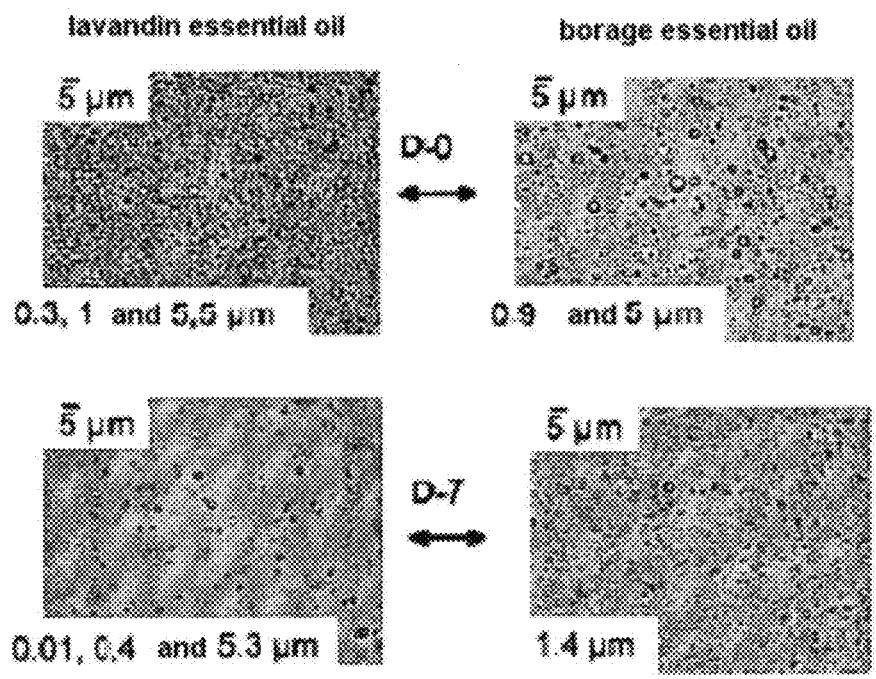
FIG. 11 represents a comparison between the optical microscopy images of the oil-in-water emulsions obtained from an aqueous solution of 100 mg/ml of β-cyclodextrin polymers (poly-β-CD) and 10 μl/ml of lavandin essential oil or of borage essential oil, on day (D-0) and seven days (D-7) after preparation of the emulsions.
Figure 12:
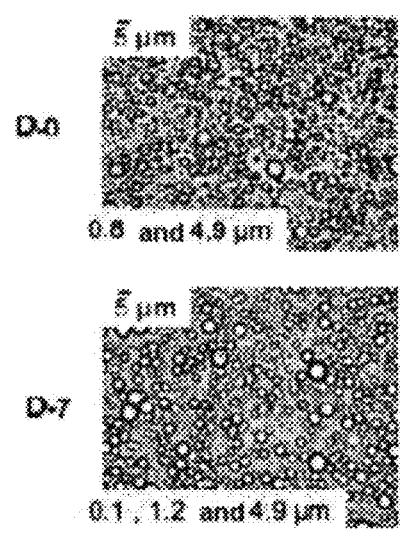
FIG. 12 represents optical microscopy images of the oil-in-water emulsions obtained from an aqueous solution of 100 mg/ml of β-cyclodextrin polymers (poly-β-CD) and 10 μl/ml of geraniol, on day (D-0) and seven days (D-7) after preparation of the emulsions.

Examination under an optical microscope and by dynamic light scattering techniques (DLS, laser particle sizing) shows that the emulsions thus prepared form very well defined, spherical droplets with a size <10 μm (FIGS. 10-12).

Generally, a large variety of products is used to stabilize emulsifying systems: surfactants, cosurfactants, organic solvents, crosslinked polymers. However, all these products have a risk of toxicity or environmental pollution related to their methods of production (heavy organic synthesis). Consequently, efforts have turned to "green" chemistry, in the use of products that are less polluting, more practical and of natural origin, while at the same time avoiding any formulation of emulsions based on surfactants, cosurfactants, organic solvents, etc.

It emerges from the above examples that the method of production of the invention makes it possible to very simply formulate a stable oil-in-water emulsion by means of a "green" process of encapsulation without the use of surfactants, cosurfactants and/or organic solvents.

Example 4

Methods for Concentrating Emulsions According to the Method of the Present Invention A concentrated cream of Parsol® MCX was prepared from an emulsion of Parsol® MCX having a total volume of 2 ml, freshly prepared, for a poly-beta-cyclodextrin concentration of 100 mg/ml and containing 10 mg/ml of Parsol® MCX (beta-cyclodextrin/Parsol® MCX molar ratio of 1/2.5). After the preparation of the emulsion in accordance with example 2, ultracentrifugation is carried out at 40 000 rpm for 15 minutes. After separation of the lower phase, a cream having a volume of 0.2 ml is thus obtained, which is equivalent to a 10-fold increase in the concentration of Parsol® MCX in the formulation (100 mg/ml). This result was confirmed by UV-VIS measurement of the lower phase where no trace of active ingredient (Parsol® MCX) was observed.

Figure 14:
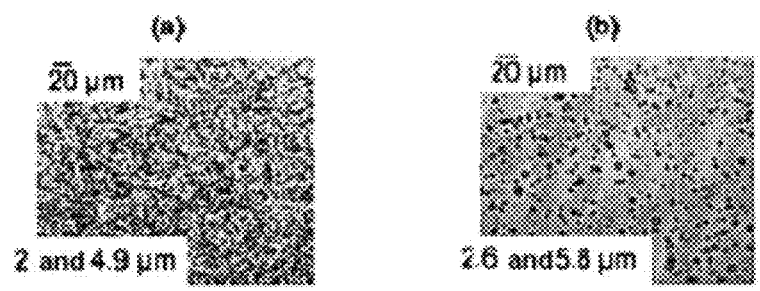
FIG. 14 represents optical microscopy images of a Parsol® MCX cream obtained after ultracentrifugation (a) and redispersion (b) of an oil-in-water emulsion obtained from 2 ml of an aqueous solution of 100 mg/ml of poly-β-cyclodextrin and 10 mg/ml of Parsol® MCX.
Figure 15:
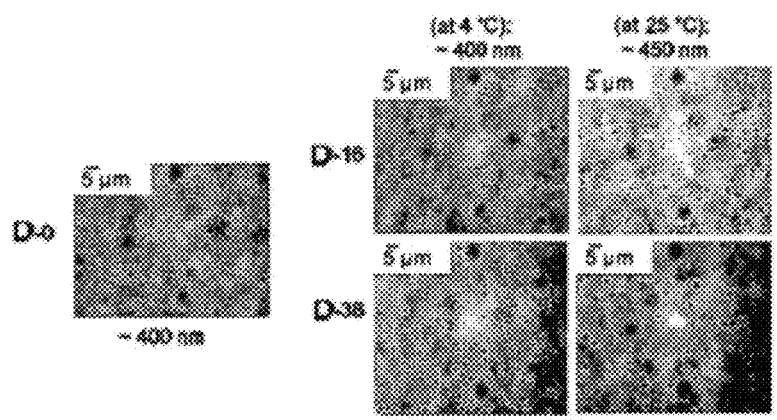
FIG. 15 represents optical microscopy images of a concentrated emulsion based on β-cyclodextrin polymer (poly-β-CD) and on geraniol (poly-β-CD/geraniol oil-in-water emulsion with an increased geraniol oil content), on the day of preparation of the concentrated emulsions (D-0) and sixteen and thirty-eight days (D-16 and D-38, respectively) after preparation of the concentrated emulsions, at 4° C. and at 25° C. The concentrated geraniol emulsions are obtained by solubilizing a β-cyclodextrin polymer having an average molar mass of $10^5$ g/mol in water at a concentration of 100 mg/ml. 50 mg of geraniol oil are added to 5 ml of the aqueous solution of poly-β-cyclodextrin thus prepared. The mixture is then subjected to pulsed sonication for 40 seconds. The resulting emulsion is subjected to ultracentrifugation at 40 000 revolutions per second for 1 hour. The resulting geraniol concentrate is separated with a Pasteur pipette (1 ml). The formation of droplets with a diameter <500 nm is observed. However, the emulsion thus formed (the geraniol concentrate) is stable over time.
Figure 16:
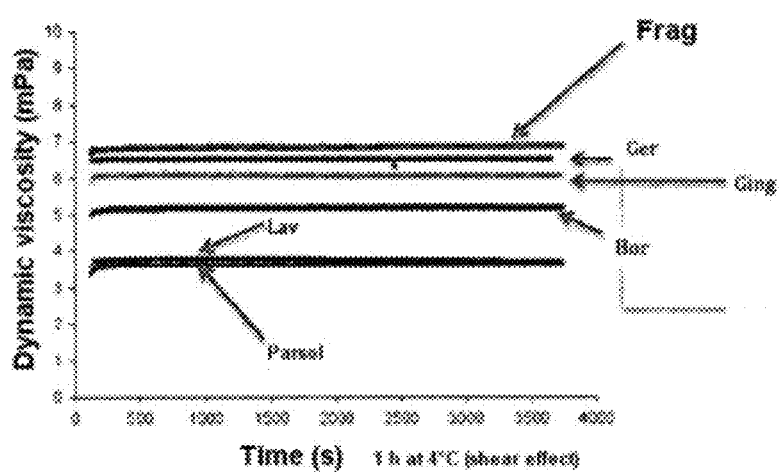
FIG. 16 represents the results obtained during a rheological study (change in dynamic viscosity (mPa) as a function of time (seconds)) carried out on oil-in-water emulsions obtained from 2 ml of an aqueous solution of β-cyclodextrin polymer (poly-β-CD) (100 mg/ml) and 10 mg/ml of borage oil (Bor), of ginger oil (Ging), of fragrance concentrate (Frag), of lavandin oil (Lav), of geraniol (Ger) or of Parsol® MCX (Parsol) at 4° C. Along the x-axis, "T" represents the time in seconds (s). Along the y-axis, "Vd" represents the dynamic viscosity in millipascals (mPa). The emulsions are obtained by solubilizing a β-cyclodextrin polymer having an average molar mass of $10^5$ g/mol in water at a concentration of 100 mg/ml. 20 mg of lipophilic active ingredient (geraniol, ginger, borage or lavandin oil, fragrance concentrate or Parsol® MCX) are added to 2 ml of the aqueous solution of poly-β-cyclodextrin thus prepared. The mixture is then subjected to pulsed sonication for 40 seconds. The emulsions thus prepared were studied with an RS600 rheological apparatus equipped with cone-plate geometry, diameter 60 mm, angle 1°, 7200 s-1; at 4° C. for a period of 3600 seconds. The results obtained indicate the remarkable stability of these emulsions (the dynamic viscosity remains constant) subjected to a shear effect for a very long period (1 hour).

Optical microscopy observation of the Parsol® MCX cream obtained after ultracentrifugation and redispersion shows that the droplet size in the cream and the emulsion after redispersion (2 and 4.9 μm) is equivalent to that of the initial emulsion (~2 and 5 μm) (FIGS. 14-*a* and *b*).

Another example of concentration was carried out with geraniol introduced into the same type of system (100 mg/ml poly-β-cyclodextrin and 11.4 mg/ml geraniol). After ultracentrifugation, a volume of 1 ml relative to the upper concentrated phase (cream) was separated for a final concentration in the system of 57 mg/ml (recovery of all of the amount of geraniol introduced).

Figure 13:
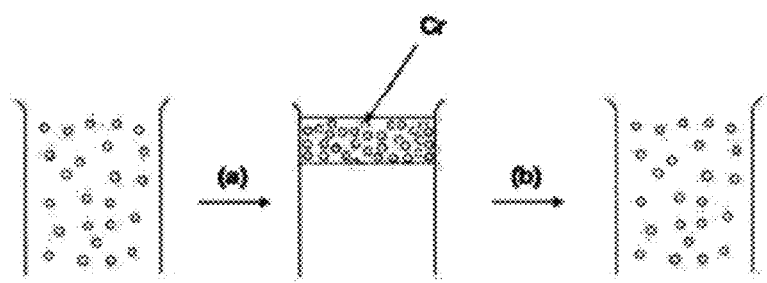
FIG. 13 represents a scheme of concentration of the emulsions by ultracentrifugation (step (a)) and redispersion (step (b)). "Cr" signifies very dense cream.

Each emulsion prepared in examples 2 and 3 can be ultracentrifuged at 40 000 revolutions per minute (rpm) for a period of time ranging from 5 minutes to 1 h and preferably to 15 minutes. It is thus possible to recover the concentrated cream and to carry out a redispersion in accordance with the scheme described in FIG. 13.

Example 5

Preparation of Sunscreen Emulsions (Formulations) (Parsol® MCX) Via the Indirect Route (Water-in-Oil) According to the Method of the Present Invention Indirect-route emulsions corresponding to a total amount equal to 2 ml of emulsion were prepared using β-cyclodextrin-based polymers having a molar mass of $10^5$ g/mol according to the following protocol:

10 mg of poly-β-CD are solubilized in 100 ml of water. 2 ml of the Parsol® MCX anti-UV agent are added to 2 ml of the aqueous solution of poly-β-CD thus prepared. The emulsion is formed by pulsed sonication for a period of 40 seconds.

Figure 17:
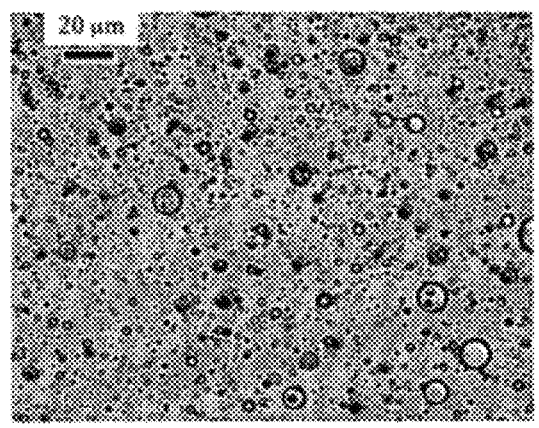
FIG. 17 represents optical microscopy images of a water-in-oil emulsion prepared from 2 ml of an aqueous solution of β-cyclodextrin polymer (poly-β-CD) having an average molar mass of $10^5$ g/mol (10 mg of poly-β-CD dissolved in 100 ml of water) and 2 ml of Parsol® MCX.
Figure 17:
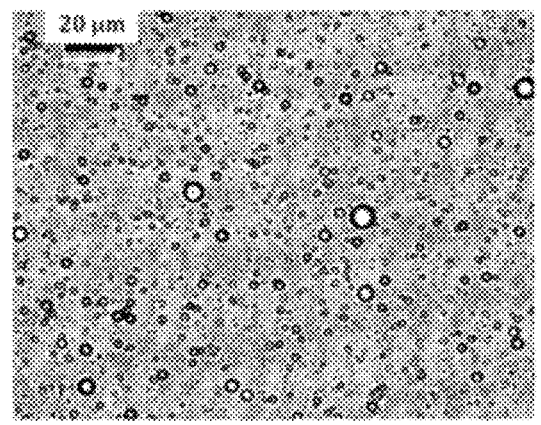

Examination under an optical microscope (observation of morphology and image analysis) shows that the emulsions thus prepared form very well defined, spherical droplets with a size <10 μm (FIG. 17).

Example 6

Freeze-Drying of Emulsions According to the Invention

Direct-route (oil-in-water) emulsions are prepared according to examples 2 to 4 above. The containers containing them are then immersed in liquid air. The emulsions are then freeze-dried for 72 hours (Bioblock Scientific Christ Alpha 1-4, vacuum 15 Pa).

Indirect-route (water-in-oil) emulsions corresponding to a total amount equal to 2 ml of emulsion were prepared using β-cyclodextrin-based polymers having a molar mass of $10^5$ g/mol:

200 mg of poly-β-CD are solubilized in 2 ml of water (100 mg/ml).

20 mg/ml of the anti-UV agent (Parsol® MCX) are added (10 mg/ml).

These emulsions were freeze-dried.

The freeze-dried materials obtained were then redispersed with 2 ml of milliQ water, so as to reconstitute the emulsions.

The diameters of the droplets before and after freeze-drying were measured: the droplet size is equivalent to that of the initial emulsion (~2 and 5 μm).

Example 7

Preparation of Emulsions (Formulations) Based on Squalene, Borage Oil and Ginger Oil Via the Direct Route (Oil-in-Water), According to the Method of the Present Invention, and Long-Term Storage of the Samples Direct-route emulsions corresponding to a total amount equal to 2 ml of emulsion were prepared using β-cyclodextrin-based polymers (poly-β-CD) having an average molar mass of $10^5$ g/mol, according to the following protocol:

100 mg/ml of (poly-β-CD) and containing, respectively:
  10 mg/ml squalene (emulsion (a)),
  10 mg/ml borage oil (emulsion (b)),
  10 mg/ml ginger oil (emulsion (c)).

Emulsions (a) to (c) are formed by pulsed sonication for a period of 40 seconds and stored at 25° C.

Figure 18:
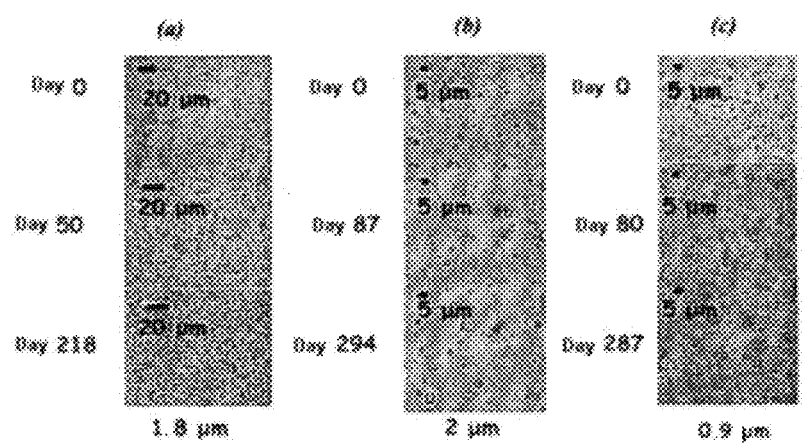
FIG. 18 represents optical microscopy images of emulsions based on β-cyclodextrin polymer (poly-β-CD), prepared according to example 7: (a) squalene; (b) ginger oil, (c) borage oil.

Optical microscopy observation of these emulsions obtained after sonication shows that the droplet size is approximately 2 μm. All these types of emulsions exhibit considerable stability over time (FIG. 18).

The interface (oil/aqueous solution of polymer) elastic behavior is measured from the variation in interfacial tension. The apparatus used for measuring the elastic properties is a Tracker®, manufactured by the company Teclis-IT Concept. The interfacial tension is measured by the drop method. A deformation of the interfacial area by dilation or by contraction of the volume of the drop creates a variation in the interfacial concentration of the polymers adsorbed at the interface. The Tracker® records the response of the interfacial tension and subsequently establishes the relationship between the deformation of the interface and this response, which describes the rheological behavior of the interface. A deformation of the interfacial area is repeated over time by imposing a sinusoidal variation in the volume of the drop, and thus makes it possible to establish the viscoelastic characteristics of the interface. The change in these characteristics makes it possible to predict the change in stability of the emulsion and to demonstrate a large number of physico-chemical phenomena. The drop is formed at the end of the capillary connected to a syringe, the plunger of which is controlled by a motor. The needle used has a 180° curve in order to have a rising drop, the density of the oils being in this case lower than that of the aqueous phase. The gauge of the needle is 18, which corresponds to an internal diameter of 0.84 mm and an external diameter of 1.27 mm. The needle is made of Teflon in order to avoid wetting of the drop on the walls of the needle. An oil drop is formed in the aqueous phase of polymers, making it possible to study the interfacial tension. The initial volume of this drop is fixed. The shape of the drop is the result of the equilibrium between capillary forces and gravity forces (Benjamins J.; Cagna A.; H., L.-R. E., *Coll. Surf. A*. 1996, 114, 245-254 [27]).

Comparative rheological studies (interfacial rheology) on this system containing 24.3 mg/ml and 100 mg/ml of poly-β-CD and also 17 mg/ml of monomer-CD confirm the hypothesis that the amount of polymer used is no longer an important parameter (see comparative example 2 carried out with Parsol® MCX).

Figure 19A:
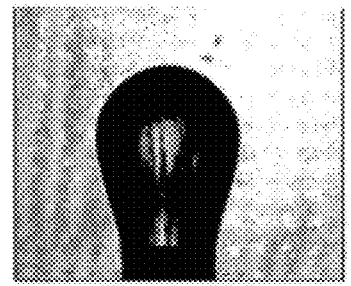
FIGS. 19A and 19B represent an interfacial rheological comparison of a drop of an emulsion prepared from squalene and (a) from an aqueous solution of β-cyclodextrin monomers (β-CD) (FIG. 19A) or (b) from an aqueous solution of β-cyclodextrin polymer (poly-β-CD) (FIG. 19B).
Figure 19B:
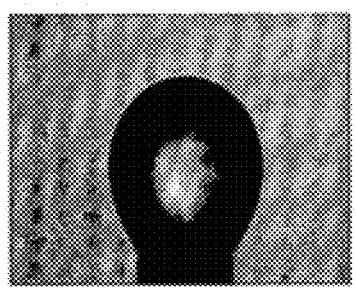
Figure 19C:
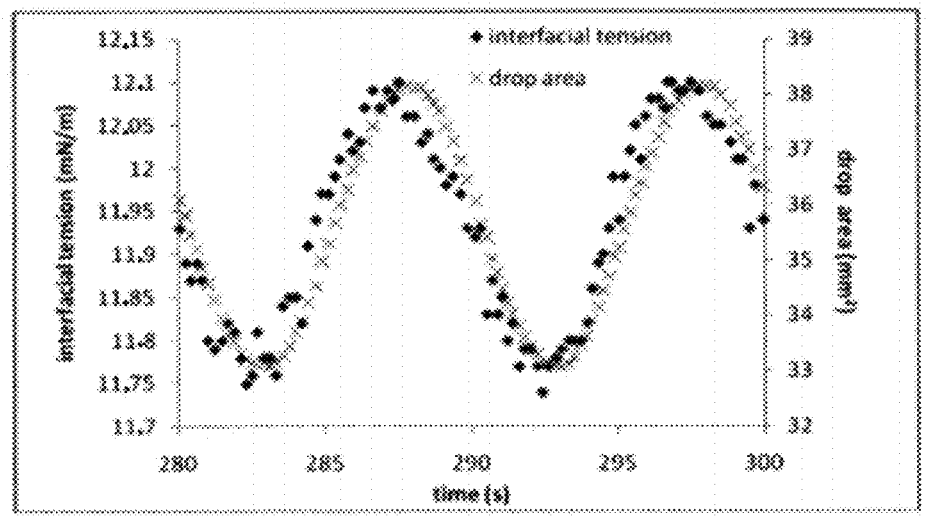
FIG. 19C represents a sinusoidal variation in interfacial tension with the volume of the drop of squalene in the squalene/β-cyclodextrin polymer (poly-β-CD) system of FIG. 19B (interfacial rheology).

In the same context, the formation of a rigid membrane at the surface of the squalene drop is observed in the case of tests carried out with an aqueous solution of β-CD monomers (FIG. 19). This fact indicates the formation of a precipitate. However, an elastic nature at the interface of the poly-β-CD and squalene/borage and ginger was observed. This indicates the strong stability of the emulsions containing more polymer (poly-β-CD) and the three oils (squalene, borage, ginger). For example, in the cases of tests carried out with squalene, the interfacial tension is approximately 12 mN/m. In this case, an increase in emulsion stability over time is observed.

Example 8

Preparation of Emulsions Based on Synthetic Sebum and Cyclodextrin (α and β) Polymers Via the Direct Route (Oil-in-Water) According to the Method of the Present Invention Emulsions containing synthetic sebum are prepared according to a protocol similar to that of example 7.

An amount of 750 mg of synthetic sebum was synthesized with the following composition, according to the protocol described in GuangWei Lu*, Satyanarayana Valiveti, Julie Spence, Christine Zhuang, Lora Robosky, Kimberly Wade, Ann Love, Lain-Yen Hu, David Pole, Matt Mollan, "Comparison of artificial sebum with human and hamster sebum samples", *International Journal of Pharmaceutics* 367 (2009) 37-43 [28]:

15% squalene, 10% palmitic acid palmitic ester, 100 oleic acid palmitic ester, 20% tripalmitin, 200 triolein, 60 oleic acid, 10% palmitic acid, 4% myristic acid, 3% cholesterol, 20 cholesterol oleate (all the products come from Sigma-Aldrich).

Several synthetic sebum emulsification tests, corresponding to a total amount equal to 2 ml of emulsion, were carried out with the CD (α and β)-based polymers in the following way:

100 mg/ml of poly-β-CD or poly-α-CD and containing the varying amounts of synthetic sebum:
  50 mg/ml (5%),
  100 mg/ml (10%).

Figure 20:
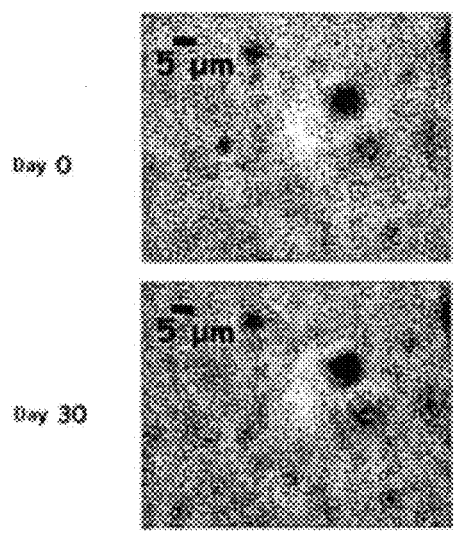
FIG. 20 represents optical microscopy images of emulsions based on synthetic sebum and on β-cyclodextrin polymer (poly-β-CD), prepared according to example 8.

The emulsions are formed by pulsed sonication for a period of 40 seconds and stored at 25° C. Optical microscopy observation of the emulsions obtained after sonication indicates an average droplet size of approximately 2 μm (FIG. 20).

Example 9

Preparation of Emulsions Based on Squalene as a Mixture with Various Essential Oils (Lemon-Grass, Linalol and Geranium Oil) and Cyclodextrin (α and β) Polymers Via the Direct Route (Oil-in-Water) According to the Method of the Present Invention Direct-route emulsions according to a protocol similar to that of example 7, corresponding to a total amount equal to 2 ml of emulsion, were prepared using α-cyclodextrin-based polymers (poly-α-CD), having a molar mass of $10^5$ g/mol, containing:

50/50 (w/w) squalene/geranium oil mixture,
50/50 (w/w) squalene/linalol mixture,
50/50 (w/w) squalene/citronella essential oil mixture.

Figure 21:
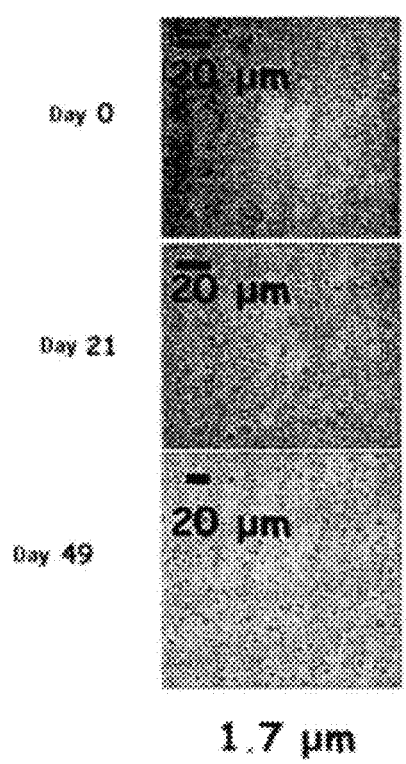
FIG. 21 represents optical microscopy images of emulsions based on squalene/geranium oil mixtures (50/50) (w/w) and α-cyclodextrin polymer (poly-α-CD), obtained according to example 9.
Figure 22:
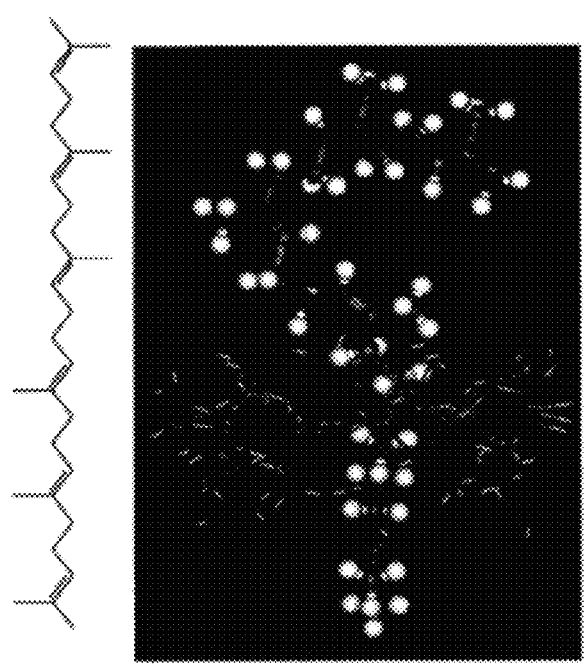
FIG. 22 represents a molecular modeling of the squalene/β-cyclodextrin polymer (poly-β-CD) host-amphiphilic guest complex.

The emulsions are formed by pulsed sonication for a period of 40 seconds and stored with tangential agitation at 25° C. Optical microscopy observation of the emulsions obtained after sonication shows that the average droplet size is approximately 2 μm (FIG. 21).

Example 10

Double-Blind Test: Skin Cleansing after Addition of Squalene

Double-blind tests for skin cleansing after addition of a drop of squalene (20 μl) were carried out with three solutions (0.5 ml for 20 seconds of cleansing):
(a) water,
(b) solution of β-CD monomer (17 mg/ml, limited by its solubility),
(c) solution of poly-β-CD (24.3 mg/ml, poly-β-CD having a % by weight of cyclodextrins of 70% CD; this is therefore a content by weight of β-CD units which is equivalent to that of the product (b) in which 17 mg/ml of β-CD monomer are used).

The three solutions were tested by a group of 10 volunteers 25 and 45 years old, after addition of a drop of squalene to the skin on the back of the hand. The skin cleansing was evaluated by the volunteers as a choice according to the following three criteria:
(1) oily sensation,
(2) less oily sensation,
(3) pleasant sensation.

All the responses obtained show rapid cleansing and a more pleasant sensation with the solution of β-cyclodextrin polymer (table 1).

TABLE 1 classification of the samples in the context of the double-blind test - skin cleaning after addition of squalene:

| Sample number | Sample composition | Classification criterion |
|---|---|---|
| (a) | Water | (1) (10 oily sensation responses) |
| (b) | Solution of β-CD monomer (17 mg/ml) | (2) (10 less oily sensation responses) |
| (c) | Solution of poly-β-CD (24.3 mg/ml) | (3) (2 less oily sensation responses) (8 pleasant sensation responses) |

Example 11

Double-Blind Test: Masking of Borage Oil Odor

Double-blind tests for masking borage oil odor were carried out with 4 different samples for 2 ml total volume, prepared as follows:

(a) borage oil (pure sample),
(b) mixture of β-CD monomer (17 mg/ml) aqueous solution and 10 mg/ml borage oil,
(c) mixture of poly-β-CD (24.3 mg/ml) aqueous solution and 10 mg/ml borage oil,
(d) poly-β-CD (solid) and 10 mg/ml borage oil.

The 4 samples were tested by a group of 8 volunteers between 25 and 50 years old. The masking of odor was graded in accordance with the following criteria:
(1) very persistent odor,
(2) persistent odor,
(3) less persistent odor,
(4) very little odor,
(5) no odor.

All the responses obtained show rapid cleansing and more pleasant sensation with the solution of poly-β-CD.

The 4 samples were classified in the following way (table 2):

TABLE 2 classification of the samples in the context of the double-blind test - masking of borage oil odor:

| Sample | Sample composition | Classification criterion |
|---|---|---|
| (a) | Borage oil (pure sample) | (2) (5 persistent odor responses) (3 less persistent odor responses) |
| (b) | Mixture β-CD monomer (17 mg/ml) aq. sol. and 10 mg/ml borage oil | (3) (7 less persistent odor responses), (1 very little odor response) |
| (c) | Mixture poly-β-CD (24.3 mg/ml) aq. sol. and 10 mg/ml borage oil | (4) (7 very little odor responses, 1 less persistent odor response) |
| (d) | Poly-β-CD (solid) and 10 mg/ml borage oil | (4) (7 very little odor responses, 1 less persistent odor response) |

LIST OF REFERENCES

[1] EP 0 685 227
[2] FR 2 858 777
[3] Duchêne et al., "Cyclodextrins and emulsions", *International Journal of Pharmaceutics*, 266 (2003), 85-90
[4] Yu et al., "Effect of camphor/cyclodextrin complexation on the stability of O/W/O multiple emulsions", *International Journal of Pharmaceutics*, 261 (2003), 1-8
[5] Inoue et al., "Emulsion preparation using β-cyclodextrin and its derivatives acting as an emulsifier", *Chem. Pharm. Bull*, 56(9), (2008), 1335-1337
[6] Inoue et al., "Formulation and characterisation of emulsions using β-cyclodextrin as an emulsifier", *Chem. Pharm. Bull*, 56(5), (2008), 668-671
[7] Inoue et al., "Preparation and characterisation of n-alkane/water emulsion stabilized by cyclodextrin", *Journal of oleo science*, 58, (2), (2009), 85-90
[8] WO 2008/003685
[9] E. Renard et al., European Polymer Journal, vol. 33, No. 1, pp 49-57 (1997)
[10] Gref et al., International Journal of Pharmaceutics, Vol. 332, Issues 1-2, pages 185-191 (2007)

[11] Gref et al., J. Control Release, 111(3): 316-24 (2006)
[12] Gref et al., Journal of colloid and interface science, 307(1): 83-93 (2007)
[13] Blanchemain et al., Acta Biomaterialia, Volume 4, Issue 6, November 2008, pages 1725-1733
[14] Elif Yilmaz Ozmen et al. *Bioresource Technology*, Volume 99, Issue 3, page 526-531 (2008)
[15] Cesteros et al., *European Polymer Journal*, Volume 45, Issue 3, page 674-679 (2009)
[16] Salmaso et al., *International Journal of Pharmaceutics*, Volume 345, Issues 1-2, pages 42-50 (2007)
[17] Yang et al., *Biomaterials*, Volume 28, Issue 21, pages 3245-3254 (2007)
[18] WO 2006/124801
[19] Prabaharan et al., *International Journal of Biological Macromolecules*, Volume 44, Issue 4, pages 320-325 (2009)
[20] Zhang et al., "Chitosan bearing pendant cyclodextrin as a carrier for controlled protein release", *Carbohydrate Polymers, In Press, Corrected Proof, Available online Jan. 30, 2009*
[21] Prabaharan et al., *Carbohydate Polymers*, Volume 73, Issue 1, pages 117-125 (2008)
[22] Prabaharan et al., *Carbohydate Polymers*, Volume 73, Issue 1, pages 117-125 (2008)
[23] Lu et al., *European Polymer Journal*, Volume 44, Issue 7, pages 2140-2145 (2008)
[24] Blanchemain et al., *Acta Biomaterialia*, Volume 4, Issue 5, pages 1392-1400 (2008)
[25] Zha et al., *Journal of Membrane Science*, Volume 321, Issue 2, pages 316-323 (2008)
[26] "Cyclodextrins and their inclusion complexes", Szejtli J., Academia Kiado, Budapest, 1982
[27] Benjamins J.; Cagna A.; H., L.-R. E., *Coll. Surf. A*. 1996, 114, 245-254
[28] GuangWei Lu*, Satyanarayana Valiveti, Julie Spence, Christine Zhuang, Lora Robosky, Kimberly Wade, Ann Love, Lain-Yen Hu, David Pole, Matt Mollan, "Comparison of artificial sebum with human and hamster sebum samples", *International Journal of Pharamceutics* 367 (2009) 37-43.

The invention claimed is:

1. An emulsion stabilized by a non-covalent and non-crystalline inclusion complex consisting essentially of (i) an aqueous solution of a cyclodextrin unit-based polymer or of a hydrophilic polymer bearing cyclodextrins; and (ii) a lipophilic compound, wherein the cyclodextrin unit-based polymer and the hydrophilic polymer bearing cyclodextrins contain at least 10 cyclodextrin units.

2. The emulsion of claim 1, wherein the polymer is chosen from the group comprising:
poly-α-, poly-β- or poly-γ-cyclodextrins,
copolymers of α-, β- and/or γ-cyclodextrins,
natural or synthetic polymers onto which α-, β- and/or γ-cyclodextrins are grafted,
or a mixture thereof;
wherein the α-, β- and/or γ-cyclodextrin units are optionally modified.

3. The emulsion of claim 1, wherein the cyclodextrin unit-based polymer comprises, on average, between 10 and 1000 cyclodextrin units within its structure.

4. The emulsion of claim 1, wherein the cyclodextrin units of the cyclodextrin polymer are bound to one another via hydrocarbon chains having the formula —O—($CH_2$—$CHOR^1$—$CH_2$)$_n$—O—, wherein n is an integer between 1 and 50 and, in each of the units ($CH_2$—$CHOR^1$—$CH_2$), $R^1$ denotes either a hydrogen atom or a —$CH_2$—CHOH—$CH_2$—O chain bound to a cyclodextrin unit of the polymer.

5. The emulsion of claim 1, wherein the cyclodextrin unit-based polymer is obtained by polycondensation of cyclodextrin and epichlorohydrin molecules.

6. The emulsion of claim 1, wherein the cyclodextrin unit-based polymer has an average molar mass between 10 000 and 3 000 000 g/mol.

7. The emulsion of claim 1, wherein the cyclodextrin unit-based polymer is a poly-β-cyclodextrin having the following structure:

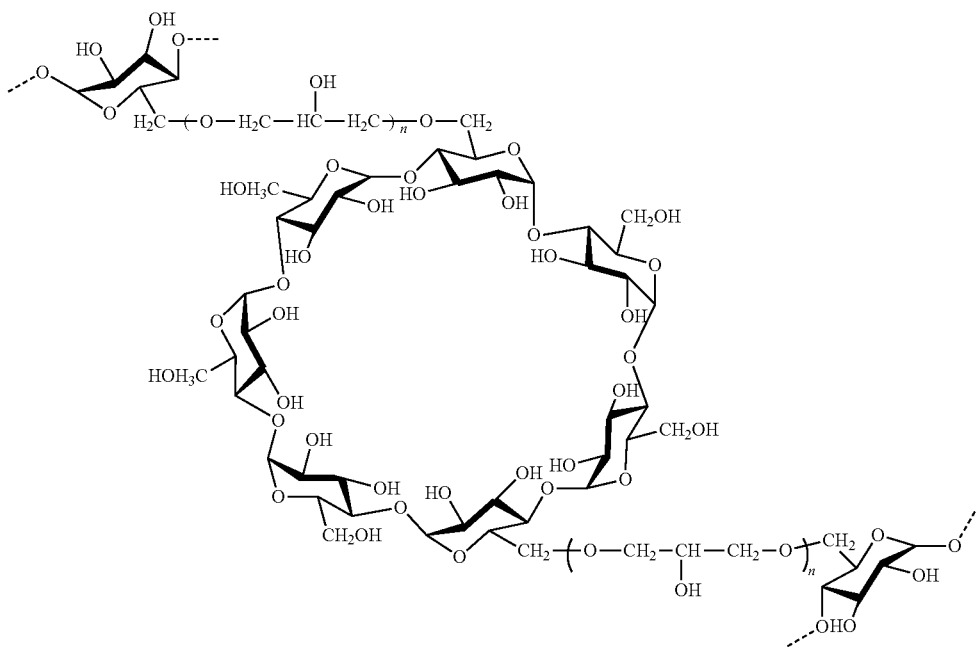

wherein n is an integer between 1 and 50; and the number of β-cyclodextrin units is, on average, between 10 and 2000 units.

8. The emulsion of claim 1, wherein the hydrophilic polymer is a polysaccharide chosen from hyaluronic acid, alginic acid, chitosan, chitin, scleroglucan, dextran, amylose, amylopectin, a cellulose derivative, starch, pullulan, pectin, an alginate, heparin, ulvan, a carrageenan, fucan, curdlan, xylan, polyguluronic acid, xanthan, arabinan and polymannuronic acid.

9. The emulsion of claim 1, wherein the lipophilic compound is selected from the group consisting of: fatty substances chosen from the group comprising natural oils of vegetable, animal or marine origin, synthetic oils, mineral oils, hydrogenated oils, silicone oils, hydrocarbon-based compounds, saturated or unsaturated fatty acids, fatty acid esters, waxes, fatty alcohols, butters, wax esters, or a mixture thereof, lipophilic odorous compounds used in the production of fragrances, and lipophilic active ingredients.

10. The emulsion of claim 9, wherein the lipophilic compound is an essential oil of vegetable, animal or marine origin, chosen from the group comprising olive oil, sesame oil, argan oil, palm oil, soybean oil, woad oil, turtle oil, babassu oil, aloe vera, avocado oil, allantoin, bisabol, grapeseed oil, apricot oil, wheatgerm oil, almond oil, arachis oil, macadamia nut oil, sea buckthorn oil, evening primrose oil, borage oil, ginger oil, geraniol, jujube oil, mink oil and lanolin; a mineral oil chosen from the group comprising isohexadecane, isoparaffin, ceresin and petrolatum; a hydrocarbon-based compound chosen from the group comprising terpenes and squalene; myristic acid as a fatty acid; a wax chosen from the group comprising whale wax, beeswax and jojoba oil; a fatty alcohol chosen from the group comprising myristyl alcohol, cetyl alcohol, stearyl alcohol, myricyl alcohol; an odorous compound used in the formulation of fragrances; or a lipophilic active ingredient chosen from emollients, anti-infectives, anticancer agents, anti-inflammatories, antibacterial agents, antifungal agents, antivirals, antiseborrheic agents, antiacne agents, antiparasitics, opioids, keratolytics, antihistamines, anesthetics, wound healing agents, pigmentation modifiers, UV-filters, free radical scavengers, moisturizers, vitamins, enzymes, or else polypeptides.

11. The emulsion of claim 10, wherein the lipophilic compound is an organic anti-UV agent.

12. A composition comprising an emulsion as defined in claim 1.

13. A method for preparing an emulsion, comprising the steps of: (i) adding a lipophilic compound to an aqueous solution of a cyclodextrin unit-based polymer or of a hydrophilic polymer bearing cyclodextrins, wherein the cyclodextrin unit-based polymer and the hydrophilic polymer bearing cyclodextrins contain at least 10 cyclodextrin units; and (ii) forming an emulsion of the mixture obtained in step (i).

14. The method of claim 13, wherein the formation of the emulsion in step (ii) is carried out by a means chosen from the group comprising sonication, homogenization by shear forces, and microfluidization.

15. The method of claim 13, wherein the lipophilic compound is added as such when it is in liquid form, or, when it is in solid form, is added in solution in a water-immiscible lipid solvent.

16. The method of claim 15, wherein the lipid solvent is Miglyol®, isopropyl myristate or squalene; or else a liquid fatty substance chosen from the group comprising natural oils of vegetable, animal or marine origin, synthetic oils, mineral oils, hydrogenated oils, silicone oil, hydrocarbon-based compounds, saturated or unsaturated fatty acids, fatty acid esters, liquid waxes, fatty alcohols, or a mixture thereof.

17. The method of claim 13, wherein the polymer is chosen from the group comprising: poly-α-, poly-β- or poly-γ-cyclodextrins, copolymers of α-, β- and/or γ-cyclodextrins, natural or synthetic polymers onto which α-, β- and/or γ-cyclodextrins are grafted, or a mixture thereof; wherein the α-, β- and/or γ-cyclodextrin units are optionally modified.

18. The method of claim 13, wherein the concentration of the cyclodextrin unit-based polymer in the aqueous solution of step (i) is between 20 and 200 mg/ml.

19. The method of claim 13, wherein the lipophilic compound is selected from the group consisting of: fatty substances chosen from the group comprising natural oils of vegetable, animal or marine origin, synthetic oils, mineral oils, hydrogenated oils, silicone oils, hydrocarbon-based compounds, saturated or unsaturated fatty acids, fatty acid esters, waxes, fatty alcohols, butters, wax esters, or a mixture thereof, lipophilic odorous compounds used in the production of fragrances, and lipophilic active ingredients.

20. The method of claim 13, wherein, in step (i), the amount of lipophilic compound is between 1 and 500 mg/ml.

21. The method of claim 13, further comprising a step of increasing the lipophilic compound content of the emulsion by ultracentrifuging said emulsion.

22. The method of claim 13, further comprising a step of freeze-drying the emulsion.

23. An encapsulation method comprising the steps of providing the emulsion of claim 1, and carrying out a concentrated encapsulation of lipophilic compounds with the emulsion.

24. A method for making a cosmetic, pharmaceutical or agri-food composition comprising the step of providing the emulsion of claim 1, and preparing the cosmetic, pharmaceutical or agri-food composition with the emulsion.

25. The method of claim 24, wherein the cosmetic composition is used for protecting the skin and/or the hair against ultraviolet radiation, in particular solar radiation.

26. A cosmetic treatment method for protecting the skin and/or the hair against ultraviolet radiation, in particular solar radiation, comprising the application, to the skin and/or the hair, of an effective amount of a composition comprising the emulsion of claim 11.

27. A method for vectorizing lipophilic compounds comprising the steps of providing the emulsion of claim 1, and vectorizing the lipophilic compounds with the emulsion.

28. An emulsion according to claim 1, wherein component (i) is an aqueous solution of a hydrophilic polymer bearing cyclodextrins wherein the hydrophilic polymer is a polysaccharide chosen from the group consisting of hyaluronic acid, alginic acid, chitosan, chitin, scleroglucan, dextran, amylose, amylopectin, a cellulose derivative, starch, pullulan, pectin, an alginate, heparin, ulvan, a carrageenan, fucan, curdlan, xylan, polyguluronic acid, xanthan, arabinan and polymannuronic acid.

* * * * *